(12) United States Patent
Galarza et al.

(10) Patent No.: US 8,778,353 B2
(45) Date of Patent: Jul. 15, 2014

(54) INFLUENZA VIRUS-LIKE PARTICLE (VLP) COMPOSITIONS

(75) Inventors: Jose M. Galarza, Scarsdale, NY (US); Demetrius Matassov, Richmond Hill, NY (US)

(73) Assignee: TechnoVax, Inc., Tarrytown, NY (US)

( * ) Notice: Subject to any disclaimer, the term of this patent is extended or adjusted under 35 U.S.C. 154(b) by 362 days.

(21) Appl. No.: 11/796,988

(22) Filed: Apr. 30, 2007

(65) Prior Publication Data

US 2008/0031895 A1 Feb. 7, 2008

Related U.S. Application Data

(60) Provisional application No. 60/798,363, filed on May 5, 2006, provisional application No. 60/796,735, filed on May 1, 2006, provisional application No. 60/796,799, filed on May 1, 2006.

(51) Int. Cl.
*A61K 39/145* (2006.01)
*C12N 7/00* (2006.01)
*C07K 14/005* (2006.01)

(52) U.S. Cl.
USPC .................. 424/209.1; 435/325; 435/69.1

(58) Field of Classification Search
None
See application file for complete search history.

(56) References Cited

U.S. PATENT DOCUMENTS

| 7,226,774 | B2 * | 6/2007 | Kawaoka | .................. 435/235.1 |
| 2005/0009008 | A1 | 1/2005 | Robinson et al. | |
| 2005/0186621 | A1 | 8/2005 | Galarza et al. | |
| 2006/0263804 | A1 | 11/2006 | Robinson et al. | |
| 2007/0184526 | A1 | 8/2007 | Smith et al. | |

FOREIGN PATENT DOCUMENTS

| WO | WO 02/00885 | * | 1/2002 |
| WO | WO 02/00885 A2 | * | 1/2002 |
| WO | WO 2005/020889 A2 | | 3/2005 |
| WO | WO 2006/135413 A2 | | 12/2006 |
| WO | WO 2007/047831 A2 | | 4/2007 |

OTHER PUBLICATIONS

Watanabe et al., "Immunogenicity and protective efficacy of replication-incompetent influenza virus-like particles," Journal of Virology, vol. 76 No. 2, pp. 767-773 (Jan. 2002).*
Horimoto et al., "Generation of Influenza A Viruses with Chimeric (Type A/B) Hemagglutinins," Journal of Virology, vol. 77 No. 14, pp. 8031-8038 (Jul. 2003).*
Salomon et al. (Mar. 20, 2006, JEM vol. 203. p. 689-697).*
Baker, et al., "Structure of Bovine and Human Papillomaviruses: Analysis by Cryoelectron Microscopy and Three-Dimensional Image Reconstruction," *Biophys J* 60:1445-1456 (1991).
Caton, et al., The Antigenic Structure of the Influenza Virus A/PR/8/34 Hemaglutinin (H1 Subtype) *Cell* 31:417-427 (1982).
Galarza, et al., "Virus-Like Particle (VLP) Vaccine Conferred Complete Protection Against a Lethal Influenza Virus Challenge," *Viral Immunol* 18(1):244-251 (2005).
Galarza, et al., "Virus-Like Particle (VLP) Vaccine Conferred Complete Protection Against a Lethal Influenza Virus Challenge," *Viral Immunol* 18(2):365-372 (2005).

(Continued)

*Primary Examiner* — Agnieszka Boesen
(74) *Attorney, Agent, or Firm* — Pasternak Patent Law; Dahna S. Pasternak

(57) ABSTRACT

Influenza virus-like particles (VLPs) comprising influenza antigenic polypeptides are described. Also described are compositions comprising these VLPs as well as methods of making and using these VLPs.

17 Claims, 13 Drawing Sheets

(56) References Cited

OTHER PUBLICATIONS

Gerhard, et al., "Antigenic Structure of Influenza Virus Haemagglutinin Defined by Hybridoma Antibodies," *Nature* 290:713-717 (1981).

Glaser, et al., "A Single Amino Acid Substitutuin in 1918 Inluenza Virus Hemagglutinin Changes Recepto Binding Specificity," *J Virol* 79(17):11533-11536 (2005).

Gomez-Puertas, et al., "Influenza Virus is the Major Driving Force in Virus Budding," *J Virol* 74(24):11538-11547 (2000).

Hagensee, et al., "Three-Dimensional Structure of Vaccinia Virus-Produced Human Papillomavirus Type 1 Capsids," *J Virol* 68(7):4503-4505 (1994).

Iwatsuki-Horimoto, et al., "The Index Influenza A Virus Subtype H5N1 Isolated from a Human in 1997 Differs in its Receptor-Binding Properties from a Virulent Avian Influenza Virus," *J General Virol* 85:1001-1005 (2004).

Latham, et al., "Formation of Wild-Type and Chimeric Influenza Virus-Like Particles Following Simultaneous Expression of Only Four Structural Proteins," *J Virol* 75(13):6154-6165 (2001).

Pushko, et al, "Influenza Virus-Like Particles Comprised of the HA, NA, and M1 Proteins of H9N2 Influenza Virus Induced Protective Immune Responses in BALB/c Mice," *Vaccine* 23:5751-5759 (2005).

Stephenson, et al., "Detection of Anti-H5 Responses in Human Sera by HI Using Horse Erythrocytes Following MF59-Adjuvented Influenza A/Duck/Singapore/97 Vaccine," *Virus Res* 103:91-95 (2004).

Thomas, et al., "Avian Influenza: A Review," *Am J Health-Syst Pharm* 64:149-165 (2007).

"Epidemiology of WHO-Confirmed Human Cases of Avian Influenza A9H5N1) Infection," World Health Organization, Geneva, *Weekly Epidemiological Record* 81(26):249-260 (2006).

* cited by examiner

```
      ATGAATCCAAATCAAAAGATAATAACAATTGGCTCTCTGTCTCTCTCACCATTGCAACAATATGCTTCCTCATGCAGATTGC
    1 ---------+---------+---------+---------+---------+---------+---------+---------+  80
      TACTTAGGTTTAGTTTTCTATTATTGTTAACCGAGAGAGAGTGGTAACGTTGTTATACGAAGGAGTACGTCTAACG
      M  N  P  N  Q  K  I  I  T  I  G  S  V  S  L  T  I  A  T  I  C  F  L  M  Q  I  A

CATCCTGGTAACTACTGTAACATTG
   81 ---------+-------+-----  105
      GTAGGACCATTGATGACATTGTAAC
      I  L  V  T  T  V  T  L
```

FIG. 13

```
      TACAAAGACTGGATCCTGTGGATTCCTTTGCCATATCATGCTTTTTGTTGTTTGCTGGGGTTCATCATGTGGGCCTGCCAGAAAGGCAACA
    1 ---------+---------+---------+---------+---------+---------+---------+---------+---------+ 100
      ATGTTTCTGACCTAGGACACCTAAGGATATGTACGAAACGGTATAGTAGCGAAAACGACCCAAGTAGTACACCCGGACGGTCTTTCCGTTGT
      y  k  d  W  I  L  W  I  S  F  A  I  S  C  F  L  C  V  V  L  L  G  F  I  M  W  A  C  Q  K  G  N  I

TTAGGTGCAACATTGCATT
  101 --------+--------+ 120
      AATCCACGTTGTAAACGTAA
      R  C  N  I  C  I
```

FIG. 14

```
atgaatccaaatcagaaaataataaccattggatcaatctgtcctggtagtcgga
 M  N  P  N  Q  K  I  I  T  I  G  S  I  C  L  V  V  G
ctaattagcctaatattgcaaataggaatataatctcaatatggattagc
 L  I  S  L  I  L  Q  I  G  N  I  I  S  I  W  I  S
```

FIG. 15

```
gattctggcgatctactcaactgtcgccagttcactggtgcttttggtctccctggggggcaatc
 I  L  A  I  Y  S  T  V  A  S  S  L  V  L  L  V  S  L  G  A  I
agtttctggatgtgttctaatggatctttgcagtgcagaatatgcatc
 S  F  W  M  C  S  N  G  S  L  Q  C  R  I  C  I
```

FIG. 16

SEQUENCE LISTING

<160> NUMBER OF SEQ ID NOS: 18

<210> SEQ ID NO 1
<211> LENGTH: 13
<212> TYPE: PRT
<213> ORGANISM: Influenza Virus A/swine/15/30 H1N1

<400> SEQUENCE: 1

Pro Glu Cys Asp Leu Leu Leu Thr Val Ser Ser Trp Ser
1               5                   10

<210> SEQ ID NO 2

```
<211> LENGTH: 13
<212> TYPE: PRT
<213> ORGANISM: Influenza Virus A 1918 H1N1

<400> SEQUENCE: 2

Pro Glu Cys Asp Leu Leu Leu Thr Ala Ser Ser Trp Ser
1               5                   10

<210> SEQ ID NO 3
<211> LENGTH: 13
<212> TYPE: PRT
<213> ORGANISM: Influenza Virus A/swine/15/30 H1N1

<400> SEQUENCE: 3

Thr Ala Ala Cys Pro Tyr Ala Gly Ala Ser Ser Phe Tyr
1               5                   10

<210> SEQ ID NO 4
<211> LENGTH: 13
<212> TYPE: PRT
<213> ORGANISM: Influenza Virus A 1918 H1N1

<400> SEQUENCE: 4

Thr Ala Ala Cys Ser Tyr Ala Gly Ala Ser Ser Phe Tyr
1               5                   10

<210> SEQ ID NO 5
<211> LENGTH: 16
<212> TYPE: PRT
<213> ORGANISM: Influenza Virus A/swine/15/30 H1N1

<400> SEQUENCE: 5

Trp Leu Val Lys Lys Glu Asn Ser Tyr Pro Lys Leu Ser Lys Ser Tyr
1               5                   10                  15

<210> SEQ ID NO 6
<211> LENGTH: 16
<212> TYPE: PRT
<213> ORGANISM: Influenza Virus A 1918 H1N1

<400> SEQUENCE: 6

Trp Leu Thr Lys Lys Gly Ser Ser Tyr Pro Lys Leu Ser Lys Ser Tyr
1               5                   10                  15

<210> SEQ ID NO 7
<211> LENGTH: 7
<212> TYPE: PRT
<213> ORGANISM: Influenza Virus A/swine/15/30 H1N1

<400> SEQUENCE: 7

Pro Lys Val Arg Gly Gln Ala
1               5

<210> SEQ ID NO 8
<211> LENGTH: 7
<212> TYPE: PRT
<213> ORGANISM: Influenza Virus A 1918 H1N1

<400> SEQUENCE: 8

Pro Lys Val Arg Asp Gln Ala
1               5

<210> SEQ ID NO 9
<211> LENGTH: 105
<212> TYPE: DNA
```

<213> ORGANISM: Influenza Virus A/Udorn/72 H3N2

<400> SEQUENCE: 9
atgaatccaa atcaaaagat aataacaatt ggctctgtct ctctcaccat tgcaacaata 60
tgcttcctca tgcagattgc catcctggta actactgtaa cattg 105

<210> SEQ ID NO 10
<211> LENGTH: 105
<212> TYPE: DNA
<213> ORGANISM: Influenza Virus A/Udorn/72 H3N2

<400> SEQUENCE: 10
tacttaggtt tagttttcta ttattgttaa ccgagacaga gagagtggta acgttgttat 60
acgaaggagt acgtctaacg gtaggaccat tgatgacatt gtaac 105

<210> SEQ ID NO 11
<211> LENGTH: 35
<212> TYPE: PRT
<213> ORGANISM: Influenza Virus A/Udorn/72 H3N2

<400> SEQUENCE: 11

Met Asn Pro Asn Gln Lys Ile Ile Thr Ile Gly Ser Val Ser Leu Thr
1 5 10 15

Ile Ala Thr Ile Cys Phe Leu Met Gln Ile Ala Ile Leu Val Thr Thr
20 25 30

Val Thr Leu
35

<210> SEQ ID NO 12
<211> LENGTH: 120
<212> TYPE: DNA
<213> ORGANISM: Influenza Virus A/Udorn/72 H3N2

<400> SEQUENCE: 12
tacaaagact ggatcctgtg gatttccttt gccatatcat gctttttgct ttgtgttgtt 60
ttgctggggt tcatcatgtg ggcctgccag aaaggcaaca ttaggtgcaa catttgcatt 120

<210> SEQ ID NO 13
<211> LENGTH: 120
<212> TYPE: DNA
<213> ORGANISM: Influenza Virus A/Udorn/72 H3N2

<400> SEQUENCE: 13
atgtttctga cctaggacac ctaaaggaaa cggtatagta cgaaaaacga aacacaacaa 60
aacgacccca agtagtacac ccggacggtc tttccgttgt aatccacgtt gtaaacgtaa 120

<210> SEQ ID NO 14
<211> LENGTH: 40
<212> TYPE: PRT
<213> ORGANISM: Influenza Virus A/Udorn/72 H3N2

<400> SEQUENCE: 14

Tyr Lys Asp Trp Ile Leu Trp Ile Ser Phe Ala Ile Ser Cys Phe Leu
1 5 10 15

Leu Cys Val Val Leu Leu Gly Phe Ile Met Trp Ala Cys Gln Lys Gly
20 25 30

Asn Ile Arg Cys Asn Ile Cys Ile
35 40

```
<210> SEQ ID NO 15
<211> LENGTH: 105
<212> TYPE: DNA
<213> ORGANISM: Influenza Virus A/PR/8/34 H1N1

<400> SEQUENCE: 15
atgaatccaa atcagaaaat aataaccatt ggatcaatct gtctggtagt cggactaatt      60
agcctaatat tgcaaatagg gaatataatc tcaatatgga ttagc                    105

<210> SEQ ID NO 16
<211> LENGTH: 35
<212> TYPE: PRT
<213> ORGANISM: Influenza Virus A/PR/8/34 H1N1

<400> SEQUENCE: 16

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser
        35

<210> SEQ ID NO 17
<211> LENGTH: 112
<212> TYPE: DNA
<213> ORGANISM: Influenza Virus A/PR/8/34 H1N1

<400> SEQUENCE: 17
gattctggcg atctactcaa ctgtcgccag ttcactggtg cttttggtct ccctgggggc      60
aatcagtttc tggatgtgtt ctaatggatc tttgcagtgc agaatatgca tc             112

<210> SEQ ID NO 18
<211> LENGTH: 37
<212> TYPE: PRT
<213> ORGANISM: Influenza Virus A/PR/8/34 H1N1

<400> SEQUENCE: 18

Ile Leu Ala Ile Tyr Ser Thr Val Ala Ser Ser Leu Val Leu Leu Val
1               5                   10                  15

Ser Leu Gly Ala Ile Ser Phe Trp Met Cys Ser Asn Gly Ser Leu Gln
            20                  25                  30

Cys Arg Ile Cys Ile
        35
```

INFLUENZA VIRUS-LIKE PARTICLE (VLP) COMPOSITIONS

CROSS REFERENCE TO RELATED APPLICATIONS

This application claims priority from U.S. Provisional Application Nos. 60/798,363, filed May 5, 2006; 60/796,735, filed May 1, 2006; and 60/796,799, filed May 1, 2006. The entire disclosures of the above-referenced applications are incorporated herein by reference.

STATEMENT AS TO FEDERALLY SPONSORED RESEARCH

Funds used to support some of the studies disclosed herein were provided by grant number 1 R43AI063830-01 awarded by the National Institute of Allergy and Infectious Disease (NIAID) of the National Institutes of Health (NIH). The U.S. Government may have certain rights in the invention.

TECHNICAL FIELD

Virus-like particles (VLPs) containing influenza antigens are described, as are methods and making and using these VLPs.

BACKGROUND

The influenza A virus is a well characterized virus that infects humans as well as a large number of other species. See, e.g., U.S. Patent Publication No. 20050186621. All of the sixteen subtypes of influenza A virus circulate in wild birds and domestic avian species. Few influenza subtypes are epidemic among humans, but periodically pandemic strains derived from animals or birds unpredictably emerge causing wide spread disease of high morbidity and mortality.

The influenza A virus (H1N1) 1918 was the most virulent and highly contagious airborne pathogen in the recorded history of human infectious diseases. After the 1918 pandemic, this virus gradually changed to a less virulent strain and with time the original highly pathogenic virus no longer circulated in humans. However, given the vast reservoir of influenza viruses in wild bird populations as well as the complex epidemiology, biology and evolutionary characteristics of this virus it is possible that a similar or related strain will reemerge creating a serious threat to global public health. In addition, the recent re-creation of this pathogen raises serious concern that the available technology could lead to reconstruction of this virus as a biological weapon.

Avian influenza viruses are also a constant threat to humans because of cross-species transmission which allows for their adaptation to humans through mutations or reassortment with the potentially of causing a global pandemic. Avian to human transmission has resulted in more than 300 human cases of avian influenza worldwide with a mortality rate close to 40%. See, Thomas & Noppenberger (2007) *Am J Health Syst Pharm.* 64(2):149-65, Epidemiology of WHO-confirmed human cases of avian influenza A(H5N1) infection. Wkly Epidemiol Rec. 2006 Jun. 30; 81(26):249-57. Indeed, since 1997, the avian influenza virus H5N1 has been causing massive disease outbreak in domestic poultry as well as in other avian and mammalian species. In addition, a recent outbreak of the highly pathogenic avian influenza subtype H7N7 in the Netherlands resulted in multiple human infections, one of which proved fatal.

Traditionally, influenza vaccines are produced in fertilized chicken eggs. Eleven days after fertilization, a single strain of influenza virus is injected into the eggs. The virus multiplies in the infected embryo and after several days of incubation, the eggs are opened the virus harvested with the fluid surrounding the embryo, purified, chemically inactivated and combined with other similarly produced strains to generate an influenza vaccine. On average, one to two eggs are needed to produce one dose of vaccine and the entire production process lasts at least six months. Given the long production times, it is unlikely that egg-based production of flu vaccines could be used to contain a flu pandemic.

Therefore, there remains a need for compositions and methods that prevent and/or treat infection with the various highly virulent and transmissible influenza strains.

SUMMARY

In one aspect, a VLP comprising at least one influenza matrix protein (M1 and/or M2), a first influenza HA protein and a first influenza NA protein, wherein the first influenza HA is selected from the group consisting of HA1, HA5 and HA7 and the first NA protein is selected from the group consisting of NA1 and NA7. In certain embodiments, the VLP includes a single matrix protein, for example M1. In other embodiments, the VLP comprises M1 and M2. In certain embodiments, the VLP comprises HA1 and NA1. In other embodiments, the VLP comprises HA7 and NA7. In still further embodiments, the VLP comprises HA5 and NA1.

Any of the VLPs described herein may further comprise an influenza nucleoprotein (NP) and/or one or two proteins of the polymerase complex (made up of PB1, PB2 and PA). For example, the VLP may include NP and/or PB1, PB2 and PA; NP and/or PB1 and PB2; NP and/or PB1 and PA; and/or NP and/or PB2 and PA.

Any of the VLPs described herein may comprise chimeric (hybrid) influenza proteins (HA, NA, M1 and/or M2). In certain embodiments, the HA and/or NA proteins are chimeric. For example, in certain embodiments, a portion of the first influenza HA protein is replaced with a homologous region from a second influenza HA protein, wherein the second influenza HA protein is derived from a different strain than the first influenza HA protein; and/or a portion of the first NA protein is replaced with a homologous region from second influenza NA protein, wherein the second influenza NA protein derived from a different strain than the first influenza NA protein. The transmembrane and/or cytoplasmic domains may be replaced with a homologous region from a different influenza protein (e.g., influenza virus A/PR/8/34 or A/Udorn/72). In certain embodiments, the transmembrane domain of a glycoprotein is replaced. In other embodiments, the cytoplasmic tail region of a glycoprotein is replaced. In yet other embodiments, the transmembrane domain and the cytoplasmic tail region of one or more glycoproteins are replaced with domains from different influenza proteins.

In another aspect, described herein is a host cell comprising any of the VLPs as described above. The host cell may be an insect, plant, mammalian, bacterial or fungal cell.

In yet another aspect, a cell stably transfected with a sequence encoding at least one influenza matrix protein or an influenza glycoprotein is provided. The cell may be an insect, plant, mammalian, bacterial or fungal cell. In certain embodiments, the cell is a mammalian cell line.

In another aspect, a packaging cell line is provided for producing influenza VLPs as described herein. The cell line is stably transfected with a sequence encoding at least one of the influenza proteins (matrix and glycoprotein) forming a VLP as described herein. Sequences encoding the remaining VLP-forming influenza proteins are introduced into the packaging cell line under conditions such that VLPs are formed. In certain embodiments, sequences encoding at least one influenza matrix protein (M1 and/or M2) are stably integrated into the packaging cell line and sequences encoding the glycoproteins expressed on the surface of the VLP are introduced into the cell such that the VLP is formed. In other embodiments, sequences encoding one or more of the glycoproteins are stably integrated into the cell to form a packaging cell line and VLPs are formed upon introduction of sequences encoding M1 and, optionally, M2. The packaging cell may be an insect, plant, mammalian, bacterial or fungal cell. In certain embodiments, the packaging cell is a mammalian cell line.

In yet another aspect, the disclosure provides an immunogenic composition comprising any of the VLPs described herein and a pharmaceutically acceptable excipient. In certain embodiments, the compositions further comprise one or more adjuvants.

In a still further aspect, a method of producing a VLP as described herein is provided, the method comprising the steps of: expressing one or more polynucleotides encoding the M1, HA and NA (and optionally M2) proteins in a suitable host cell under conditions such that the VLPs assemble in the host cell; and isolating the assembled VLPs from the host cell. The host cell can be a mammalian cell, an insect cell, a yeast cell or a fungal cell. In certain embodiments, an expression vector comprising one or more polynucleotides operably linked to control elements compatible with expression in the selected host cell are introduced into the host cell. The expression vector may be a plasmid, a viral vector, a baculovirus vector or a non-viral vector. In certain embodiments, one or more of the polynucleotides are stably integrated into the host cell. Alternatively, one or more of the polynucleotides may be transiently introduced into the host cell.

In another aspect, provided herein is a method of generating an immune response in a subject to one or more influenza viruses, the method comprising the step of administering a composition comprising one or more VLPs as described herein to the subject. In certain embodiments, the composition is administered intranasally. Any of the methods may involve multiple administrations (e.g., a multiple dose schedule). Furthermore, any of the methods described herein may generate an immune response to more than one influenza virus strain.

BRIEF DESCRIPTION OF THE DRAWINGS

FIG. 13 depicts the nucleotide (SEQ ID NOs:9 and 10) and amino acid sequence (SEQ ID NO:11) of amino terminus of A/Udorn/72 (H3N2) Neuraminidase (NA) protein, including the cytoplasmic tail and transmembrane domains. The NA cytoplasmic tail contains six N-terminal residues (MNPNQK, shown in bold) (residues 1 to 6 of SEQ ID NO:11) which are identical sequence almost all nine known NA subtypes. The transmembrane domain is underlined.

FIG. 14 depicts the nucleotide (SEQ ID NOs:12 and 13) and amino acid sequence (SEQ ID NO:14) of amino terminus of A/Udorn/72 hemagglutinin (HA) protein, including the cytoplasmic tail and transmembrane domains. The HA cytoplasmic tail contains 10-12 residues (QKGNIRCNICI, shown in bold) (residues 30 to 40 of SEQ ID NO:14) which are highly conserved between influenza strains. The transmembrane domain is underlined and three residues of the ectodomain (YKD, residues 1-3 of SEQ ID NO:14) are shown in lower case.

FIG. 15 depicts the nucleotide (SEQ ID NO:15) and amino acid sequence (SEQ ID NO:16) of amino terminus of influenza A/PR/8/34 (H1N1) Neuraminidase (NA) protein, including the cytoplasmic tail and transmembrane domains. The NA cytoplasmic tail contains six N-terminal residues (MNPNQK, shown in bold) (residues 1 to 6 of SEQ ID NO:16) which are identical sequence almost all nine known NA subtypes. The transmembrane domain is underlined.

FIG. 16 depicts the nucleotide (SEQ ID NO:17) and amino acid (SEQ ID NO:18) sequence of amino terminus of A/PR/8/34 hemagglutinin (HA) protein, including the cytoplasmic tail and transmembrane domains. The HA cytoplasmic tail (SNGSLQCRICI, residues 27 to 37 of SEQ ID NO:18) is shown in bold and the transmembrane domain is underlined.

DETAILED DESCRIPTION

Figure 1:
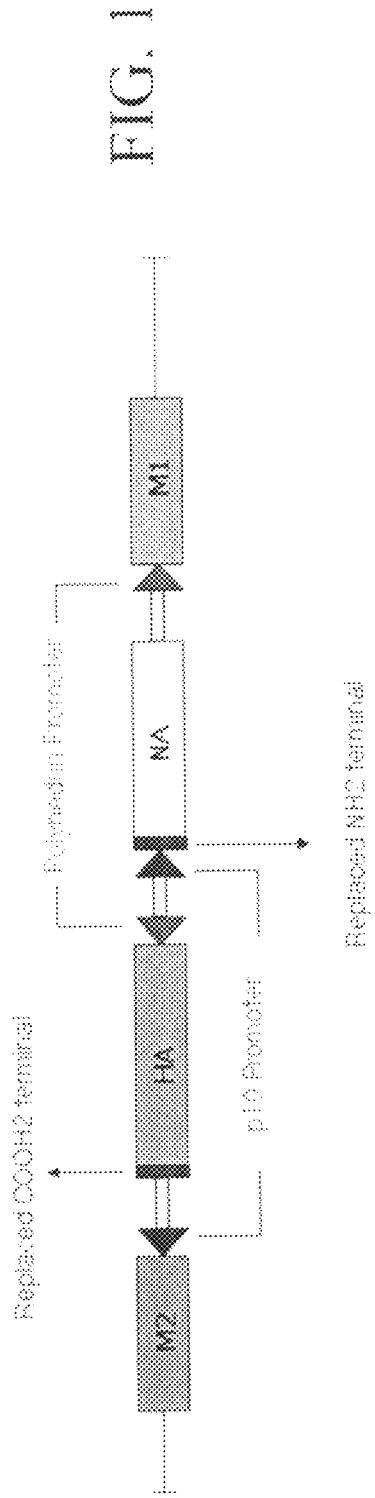
FIG. 1 is a schematic diagram showing of the position and orientation of the four influenza genes contained in the quadruple baculovirus recombinant construct. Expression of the HA and NA of the 1918 influenza A virus together with the M1 and M2 proteins derived from the influenza virus A/Udorn/73 results in VLP formation. The transmembrane domains and cytoplasmic tails of the 1918 HA and NA were replaced by those of the influenza A/Udorn virus glycoproteins (NH2 terminal in NA and COOH terminal in HA). In this construct, the HA and M1 genes are in opposite orientation to each other and under the transcriptional control of the baculovirus polyhedrin promoter whereas the M2 and NA are under the transcriptional control of the p 10 promoter and in opposite orientation to each other.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag).

All publications, patents and patent applications cited herein are hereby incorporated by reference in their entirety.

As used in this specification and the appended claims, the singular forms "a," "an" and "the" include plural references unless the content clearly dictates otherwise. Thus, for example, reference to "a VLP" may include a mixture of two or more such VLPs.

Definitions

As used herein, the terms "sub-viral particle" "virus-like particle" or "VLP" refer to a nonreplicating, viral shell, preferably derived entirely or partially from influenza virus proteins. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding (e.g., Examples). Alternatively, cryoelectron microscopy can be performed on vitrified aqueous samples of the VLP preparation in question, and images recorded under appropriate exposure conditions.

By "particle-forming polypeptide" derived from a particular viral (e.g., influenza) protein is meant a full-length or near full-length viral protein, as well as a fragment thereof, or a viral protein with internal deletions, insertions or substitutions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, vatine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, see e.g., McCaughan et al. (1995) *PNAS USA* 92:5431-5435; Kochetov et al (1998) *FEBS Letts.* 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of one or more sequences of interest in a host cell. Thus, the term includes cloning and expression vehicles, as well as viral vectors. The term is used interchangeable with the terms "nucleic acid expression vector" and "expression cassette."

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

General Overview

Described herein are virus-like particles (VLPs) comprising one or more influenza proteins (e.g., glycoproteins, structural proteins, etc), compositions comprising these VLPs, as well as methods for making and using these VLPs. The VLPs preferably comprise influenza matrix (M1 and/or M2) proteins and influenza glycoproteins (hemagglutinin (HA) and/or neuraminidase (NA)). In certain embodiments, the VLPs comprise surface glycoproteins (e.g., HA and/or NA) from the 1918 influenza strain, the avian influenza virus A/Netherland/2003 (N7N7) and/or the avian influenza A virus H5N1. Methods of making and using these compositions are also described.

VLPs are structures that morphologically resemble an influenza virus, but are devoid of the genetic material required for viral replication and infection. Using VLPs rather than inactivated influenza virus for the production of VLP vaccines has several advantages, including ease of production and purification, as compared current vaccines which are manufactured in eggs. Influenza VLP vaccine compositions may also avoid or reduce the unwanted side effects of current inactivated, egg-based vaccines seen in young children, elderly, and people with allergies to components of eggs. Furthermore, unlike many inactivated influenza virus vaccines, the HA and NA proteins of the VLPs described herein maintain conformational epitopes involved in eliciting protective neutralizing antibody responses.

When sequences encoding influenza proteins are expressed in eukaryotic, the proteins have been shown to self-assemble into noninfectious virus-like particles (VLP). See, Latham & Galarza (2001) *J. Virol.* 75(13):6154-6165; Galarza et al. (2005) *Viral. Immunol.* 18(1):244-51; and U.S. Patent Publications 20050186621 and 20060263804. Thus, the use of VLP technology allows for the safe creation of vaccines against extremely dangerous pathogens such as various human and avian influenza viruses.

Virus-Like Particles

1. Influenza Polypeptide-Encoding Sequences

The VLPs produced as described herein are conveniently prepared using standard recombinant techniques. Polynucleotides encoding the influenza proteins are introduced into a host cell and, when the influenza proteins are expressed in the cell, they assemble into VLPs.

Polynucleotide sequences coding for molecules (structural and/or antigen polypeptides) that form and/or incorporated into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and the released DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

The influenza VLPs described herein are typically formed by expressing sequences encoding one or more influenza matrix proteins (M1 and, optionally, M2) and one or more antigenic influenza glycoproteins (HA and NA) in a host cell. The expressed proteins self-assemble into VLPs with the antigenic glycoproteins decorating the surface of the VLP.

The VLPs described herein may further comprise an influenza nucleoprotein (NP) and/or at least one protein of the polymerase complex, i.e., one or more of PB1, PB2 and PA (e.g., PB1, PB2, and PA; PB1 and PB2; PB1 and PA; PB2 and PA). Preferably, the VLPs do not include NP and all three proteins of the polymerase complex. The structure and function of influenza NP and polymerase complex proteins is known and described for example on pages 428 to 432 of Kuby Immunology, $4^{th}$ ed. (Goldsby et al. eds.) WH Freeman & Company, New York.

The sequences may encode naturally occurring or modified (e.g., by deletions, additions and/or substitutions) influenza polypeptides and may be obtained from any influenza virus strain. (see, Examples). For example, in certain embodiments, the sequences encoding the matrix protein(s) are derived from the influenza virus strain A/Udorn/72 (H3N2 or A/PR/8 (H1N1) and the glycoproteins are derived from the 1918 influenza A virus strain (H1N1); avian influenza virus A/Mallard/Netherlands/2000 (H7N7); or avian influenza virus A/Vietnam/1203/2004 (H5N1).

In certain embodiments, the glycoprotein sequences encode chimeric polypeptides, for example influenza chimeric glycoproteins in which all or part (s) of the glycoproteins are replaced with sequences from other viruses and/or sequences from other influenza strains. In a preferred embodiment, the chimeric glycoprotein-encoding sequences are modified such that the transmembrane and/or cytoplasmic tail domains are encoded by sequences derived from a different influenza strain than the strain from which the antigenic portion of the glycoprotein decorating the surface of the VLP is derived. See, FIG. 12 and FIGS. 13 to 16. For example, the transmembrane domain and cytoplasmic tail of both HA and NA may be replaced by the homologous domains derived from influenza A/PR/8/34 (H1N1) or A/Udorn/72 (H3N2). The HA molecule is a type I glycoprotein, thus the transmembrane and cytoplasmic tail exchanged are located at the carboxyl-terminal ($COOH_2$) end of the molecule. In the case of NA, a type II glycoprotein, the exchanged domains are located at the amino-terminal ($NH_2$) end of the molecule (FIG. 12). These exchanges enhance the interaction of the surface glycoproteins with the scaffold formed by the matrix protein M1, which is derived from either influenza AIPR/8/34 or A/Udorn/72 virus and underlies the membrane of the sub-viral structure (FIGS. 11 to 16).

Preferably, the influenza sequences employed to form influenza VLPs exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring influenza polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring influenza polynucleotide sequence.

Any of the sequences described herein may further include additional sequences. For example, to further to enhance vaccine potency, hybrid molecules are expressed and incorporated into the sub-viral structure. These hybrid molecules are generated by linking, at the DNA level, the sequences coding for the M1 or M2 genes with sequences coding for an adjuvant or immuno-regulatory moiety. During sub-viral structure formation, these chimeric proteins are incorporated into or onto the particle depending on whether M1 or optionally included M2 carries the adjuvant molecule. The incorporation of one or more polypeptide immunomodulatory polypeptides (e.g., adjuvants describe in detail below) into the sequences described herein into the VLP may enhance potency and therefore reduces the amount of antigen required for stimulating a protective immune response. Alternatively, as described below, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors.

2. Expression Vectors

Once the constructs comprising the sequences encoding the influenza polypeptides desired to be incorporated into the VLP have been synthesized, they can be cloned into any suitable vector or replicon for expression. Numerous cloning vectors are known to those of skill in the art, and one having ordinary skill in the art can readily select appropriate vectors and control elements for any given host cell type in view of the teachings of the present specification and information known in the art about expression. See, generally, Ausubel et al, supra or Sambrook et al, supra.

Non-limiting examples of vectors that can be used to express sequences that assembly into VLPs as described herein include viral-based vectors (e.g., retrovirus, adenovirus, adeno-associated virus, lentivirus), baculovirus vectors (see, Examples), plasmid vectors, non-viral vectors, mammalian vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, enhancer, exon, intron, splicing sites translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9):815-821, 1994; Kozak, M., J Cell Biol 108 (2):229-241, 1989; Kozak, M., and Shatkin, A. J., Methods Enzymol 60:360-375, 1979).

For example, typical promoters used for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs as described herein (Chapman et al., Nuc. Acids Res. (1991) 19:3979-3986).

Enhancer elements may also be used herein to increase expression levels of the constructs, for example in mammalian host cells. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

It will be apparent that a vector may contain one or more sequences as described herein. For example, a single vector may carry sequences encoding all the proteins found in the VLP. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector.

In addition, one or more sequences encoding non-influenza proteins may be expressed and incorporated into the VLP, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

3. VLP Production

As noted above, influenza proteins expressed in a eukaryotic host cell have been shown to self-assemble into noninfectious virus-like particles (VLP). Accordingly, the sequences and/or vectors described herein are then used to transform an appropriate host cell. The construct(s) encoding the proteins that form the VLPs described herein provide efficient means for the production of influenza VLPs using a variety of different cell types, including, but not limited to, insect, fungal (yeast) and mammalian cells.

Preferably, the sub-viral structure vaccines are produced in eukaryotic cells following transfection, establishment of continuous cell lines (using standard protocols as known to one skilled in the art) and/or infection with DNA molecules that carry the influenza genes of interest. The level of expression of the proteins required for sub-viral structure formation is maximized by sequence optimization of the eukaryotic or viral promoters that drive transcription of the selected genes. The sub-viral structure vaccine is released into the culture medium, from where it is purified and subsequently formulated as vaccine. The sub-viral structures are not infectious vaccines and therefore vaccine inactivation is not required.

The ability of influenza polypeptides expressed from sequences as described herein to self-assemble into VLPs with antigenic glycoproteins presented on the surface allows these VLPs to be produced in any host cell by the co-introduction of the desired sequences. The sequence(s) (e.g., in one or more expression vectors) may be stably and/or transiently integrated in various combinations into a host cell.

Suitable host cells include, but are not limited to, bacterial, mammalian, baculovirus/insect, yeast, plant and *Xenopus* cells.

For example, a number of mammalian cell lines are known in the art and include primary cells as well as immortalized cell lines available from the American Type Culture Collection (A.T.C.C.), such as, but not limited to, BHK, VERO, HT1080, MRC-5, WI 38, MDCK, MDBK, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

Similarly, bacterial hosts such as *E. coli, Bacillus subtilis*, and *Streptococcus* spp., will find use with the present expression constructs.

Yeast hosts useful in the present disclosure include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Fungal hosts include, for example, *Aspergillus*.

Insect cells for use with baculovirus expression vectors include, inter alia, *Aedes aegypti, Autographa californica, Bombyx mori, Drosophila melanogaster, Spodoptera frugiperda*, and *Trichoplusia ni*. See, Latham & Galarza (2001) J. Virol. 75(13):6154-6165; Galarza et al. (2005) *Viral. Immunol.* 18(1):244-51; and U.S. Patent Publications 20050186621 and 20060263804.

Cell lines expressing one or more of the sequences described above can readily be generated given the disclosure provided herein by stably integrating one or more sequences (expression vectors) encoding the influenza proteins of the VLP. See, Example 7. The promoter regulating expression of the stably integrated influenza sequences (s) may be constitutive or inducible. Thus, a cell line can be generated in which one or more both of the matrix proteins are stably integrated such that, upon introduction of the influenza glycoprotein-encoding sequences described herein (e.g., chimeric glycoproteins) into a host cell and expression of the influenza proteins encoded by the polynucleotides, non-replicating influenza viral particles that present antigenic glycoproteins are formed.

Example 7 describes the production of a mammalian (CHO) cell line that was generated to express an influenza HA glycoprotein. Sequences encoding a matrix protein (M1 and/or M2) and/or NA can be introduced into such a cell line to produce VLPs as described herein. Alternatively, a cell line that stably produces influenza M1 and, optionally, M2 proteins can be generated and sequences encoding the glycoprotein(s) from the selected influenza strain introduced into the cell line, resulting in production of VLPs presenting the desired antigenic glycoproteins.

The parent cell line from which an influenza VLP-producer cell line is derived can be selected from any cell described above, including for example, mammalian, insect, yeast, bacterial cell lines. In a preferred embodiment, the cell line is a mammalian cell line (e.g., 293, RD, COS-7, CHO, BHK, VERO, MRC-5, HT1080, and myeloma cells). Production of influenza VLPs using mammalian cells provides (i) VLP formation; (ii) correct myristylation, glycosylation and budding; (iii) absence of non-mammalian cell contaminants and (iv) ease of purification.

In addition to creating cell lines, influenza-encoding sequences may also be transiently expressed in host cells. Suitable recombinant expression host cell systems include, but are not limited to, bacterial, mammalian, baculovirus/insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.)), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media Pa.; Clontech), expression in yeast (Rosenberg, S, and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997).

Figure 11:
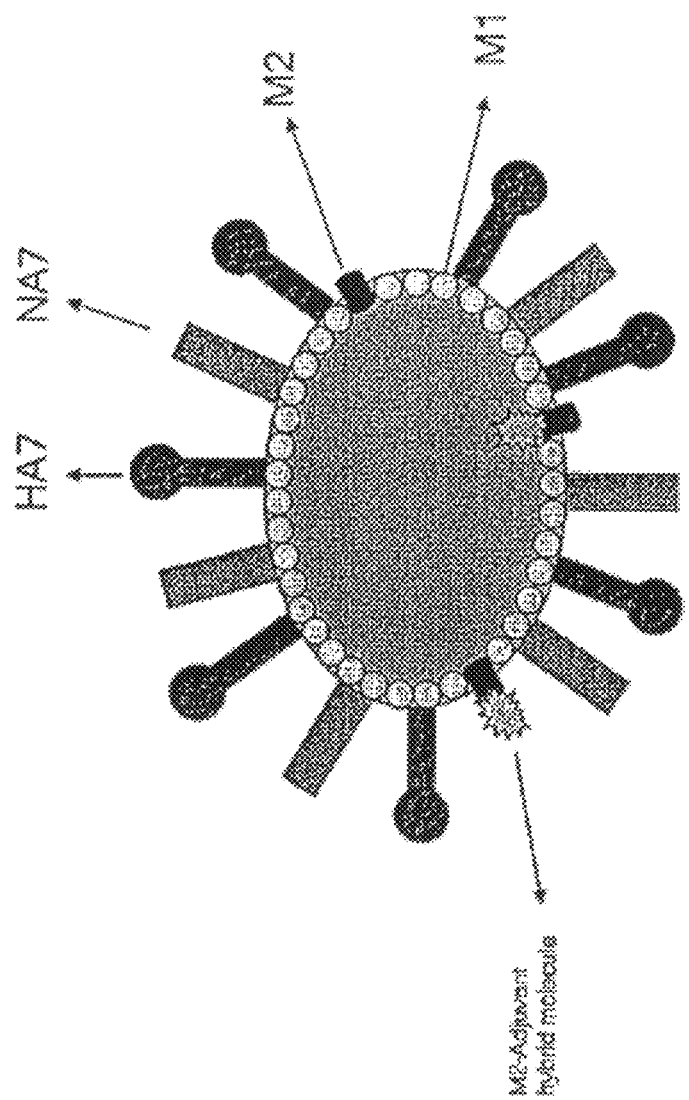
FIG. 11 is a schematic depicting the structure of exemplary sub-viral structures (VLPs) as described herein. The matrix M1 protein underlines the membrane of the structure and chimeric glycoproteins HA (e.g., HA1, HA5 and/or HA7) and NA (e.g., NA1 and/or NA7) decorate the surface of the particle. The M2 protein spans the membrane and may carry adjuvant molecule(s) linked to either the internal carboxyl or external amino terminus.
Figure 12:
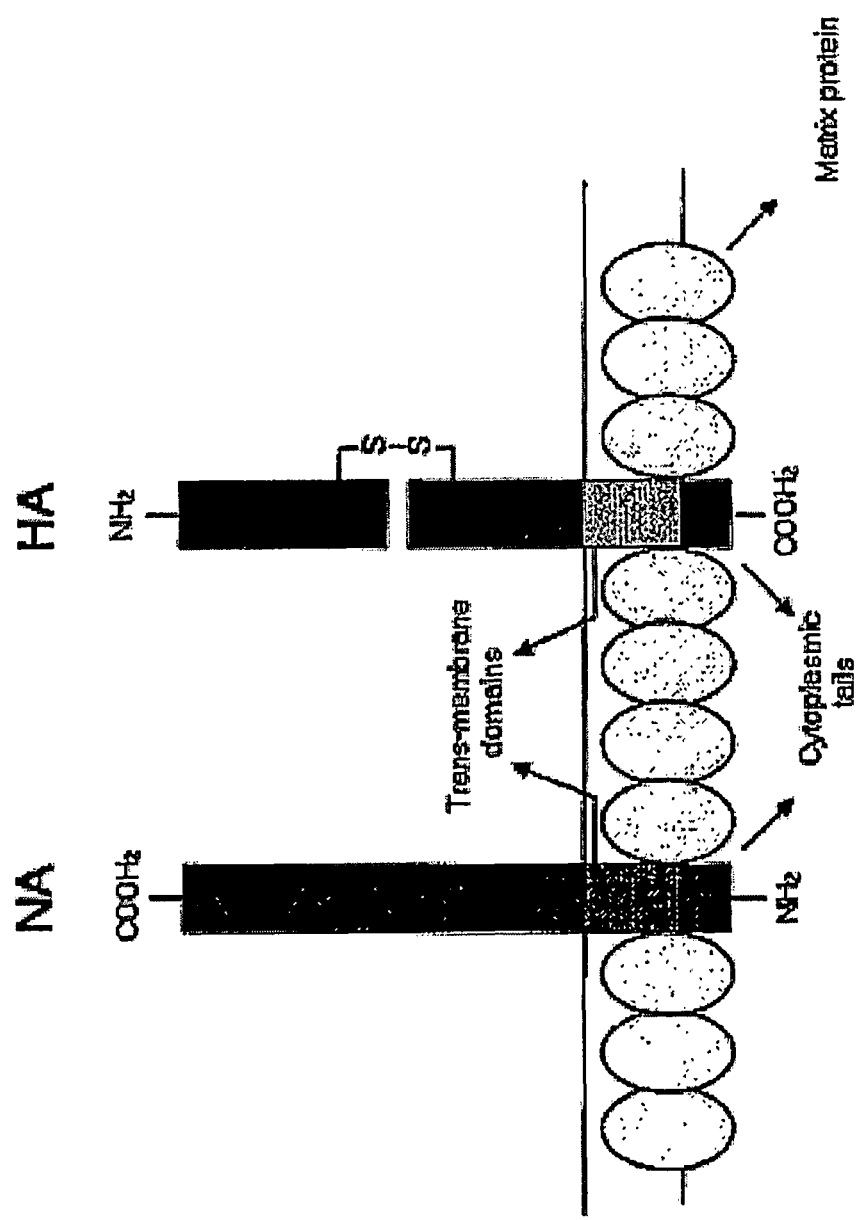
FIG. 12 is a schematic depicting exemplary chimeric HA and NA glycoproteins in which the transmembrane and cytoplasmic domains of the selected HA and NA proteins are replaced with sequences from influenza virus A/PR/8/34.

When expression vectors containing the altered genes that code for the proteins required for sub-viral structure vaccine formation are introduced into host cell(s) and subsequently expressed at the necessary level, the sub-viral structure vaccine assembles and is then released from the cell surface into the culture media (FIG. 11).

Depending on the expression system and host selected, the VLPs are produced by growing host cells transformed by an expression vector under conditions whereby the particle-forming polypeptides are expressed and VLPs can be formed. The selection of the appropriate growth conditions is within the skill of the art. If the VLPs are accumulate intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose gradients, PEG-precipitation, pelleting, and the like (see, e.g., Kimbauer et al. J. Virol. (1993) 67:6929-6936), as well as standard purification techniques including, e.g., ion exchange and gel filtration chromatography.

Compositions

VLPs produced as described herein can be used to elicit an immune response when administered to a subject. As discussed above, the VLPs can comprise a variety of antigens (e.g., one or more influenza antigens from one or more strains or isolates). Purified VLPs can be administered to a vertebrate subject, usually in the form of vaccine compositions. Combination vaccines may also be used, where such vaccines contain, for example, other subunit proteins derived from influenza or other organisms and/or gene delivery vaccines encoding such antigens.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 10 (or more) mg, more preferably about 1 µg to about 300 µg, of VLP/antigen.

Sub-viral structure vaccines are purified from the cell culture medium and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

A carrier is optionally present in the compositions described herein. Typically, a carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J P, et al., J. Microencapsul. 14(2):197-210, 1997; O'Hagan D T, et al., Vaccine 11(2):149-54, 1993. Such carriers are well known to those of ordinary skill in the art.

Additionally, these carriers may function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b)

SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulomm. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) *J. Immunology* 144:290-298, Weber et al. (1987) *J. Exp. Med.* 166:1716-1733, Gansbacher et al. (1990) *J. Exp. Med.* 172:1217-1224, and U.S. Pat. No. 4,738,927-); IL-3 and IL-4 (Tepper et al. (1989) *Cell* 57:503-512, Golumbek et al. (1991) *Science* 254:713-716, and U.S. Pat. No. 5,017,691); IL-5 and IL-6 (Brakenhof et al. (1987) *J. Immunol.* 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) *Methods in Enz.* 78:387-394, Twu et al. (1989) *Proc. Natl. Acad. Sci. USA* 86:2046-2050, and Faktor et al. (1990) *Oncogene* 5:867-872); β-interferon (Seif et al. (1991) *J. Virol.* 65:664-671); γ-interferons (Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942-951); CD3 (Krissanen et al. (1987) *Immunogenetics* 26:258-266); ICAM-1 (Altman et al. (1989) *Nature* 338:512-514, Simmons et al. (1988) *Nature* 331:624-627); ICAM-2, LFA-1, LFA-3 (Wallner et al. (1987) *J. Exp. Med.* 166:923-932); MHC class I molecules, MHC class II molecules, B7.1-β2-microglobulin (Parnes et al. (1981) *Proc. Natl. Acad. Sci. USA* 78:2253-2257); chaperones such as calnexin; and MHC-linked transporter proteins or analogs thereof (Powis et al. (1991) *Nature* 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids encoding one or more of the above-identified polypeptides can be digested with appropriate restriction enzymes, and DNA fragments containing the particular gene of interest can be inserted into a gene transfer vector (e.g., expression vector as described above) using standard molecular biology techniques. (See, e.g., Sambrook et al., supra, or Ausubel et al. (eds) Current Protocols in Molecular Biology, Greene Publishing and Wiley-Interscience).

Administration

The VLPs and compositions comprising these VLPs can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration. Multiple doses can be administered by the same or different routes. In a preferred embodiment, the doses are intranasally administered.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting. For instance, although the VLPs disclosed in the Examples include M2, it will be apparent from the above disclosure that M2 is optional and that influenza VLPs as described herein can be formed without M2. See, also, U.S. Patent Publication Nos. 20050186621 and 20060263804.

EXAMPLES

Example 1

Generation of a Baculovirus Transfer Vector

The HA gene of the influenza virus A/South Carolina/1/1918 (H1N1) (GenBank Accession #AF117241) was de novo synthesized with the following modifications: 1) the 3' terminus which encodes the transmembrane domain and cytoplasmic tail were replaced with the analogous domains of the HA3 of influenza A/Udorn/72 (H3N1), 2) the Not I, Kpn I restriction sites as well as the T7 polymerase promoter sequence were added at the 5' terminus of gene whereas Avr II and Not I were added to the 3' terminus.

The nucleotide sequence of the A/Brevig_Mission/1/1918 (H1N1) neuraminidase (NA) gene (GenBank Accession #AF250356) was also de novo synthesized with the following changes: 1) the 5' terminus encoding the NH2-terminal cytoplasmic tail and transmembrane anchoring domain were replaced with those of the NA1 of influenza A/Udorn/72 (H3N1), 2) the Sma I and Asc I restriction sites were added to the 5' end of the gene whereas the FseI, Sma I and Not I were added at the 5' terminus. The NA gene was sub-cloned via the Sma I site into the intermediate shuttle vector as described in Latham & Galarza (2001) *J. Virol.* 75(13):6154-6165 and U.S. Patent Publications 20050186621, which carries the M1 gene. In this intermediate construct, the NA gene is positioned under the transcriptional control of the baculovirus p10 promoter and the M1 gene under the transcriptional control of the polyhydron promoter.

These M1 and NA1 genes and respective promoters were cut out as a single fragment by digesting the shuttle vector with PmeI and SacI restriction enzymes. The M1-NA insert was then sub-cloned into the PmeI/ SacI sites of the baculovirus transfer vector pAcab4-M2 (Latham & Galarza (2001) *J. Virol.* 75(13):6154-6165 and U.S. Patent Publication 20050186621, which contains the M2 gene was already cloned.

Subsequently, the 1918 HA (HA1N1) gene was sub-cloned into the pAcAB4-M2-M1-NA via the Not I site. Restriction enzyme analysis was used to select the plasmids that carried the HA gene in the correct orientation with respect the polyhedron promoter. The selected pAcAB4-M2-1918HA-1918NA-M1 plasmid was amplified, purified using an endotoxin-free plasmid purification kit from Qiagen, Valencia, Calif. and sequenced to verify the genes and promoters nucleotide sequence as well as the genes orientation.

In this final construct, the M1 and 1918HA genes are under the control of the polyhedrin promoter and in opposite direction whereas the M2 and 1918NA are also in opposite direction to each other and under the control of the p10 promoter (FIG. 1).

Example 2

Generation of a Baculovirus Recombinant Virus that Produces the 1918 Virus-Like Particles (VLP)

To create a baculovirus recombinant, Sf9 insect cells were seeded at a density of ~2×10$^6$ onto 60 mm dishes and subsequently transfected with a mixture of ~2 μg of the 1918-transfer vector and 0.5 μg of linearized BaculoGold Bright™ baculovirus DNA, BD Biosciences Pharmagin (San Diego, Calif.). This linear baculovirus DNA carries within its genome the green fluorescence protein (GFP) gene, therefore the infectious virus generated by homologous recombination within the insect cells expresses the GFP in addition to the influenza proteins required for VLP assembly. The GFP protein serves as a marker for recognizing and selecting virus recombinants as well as for accurate determination of virus titers and multiplicity of infections.

GFP producing baculovirus recombinants were selected, expanded, and analyzed by PCR and Western blot to verify the presence of the four genes and their expression respectively. The selected recombinant virus was amplified and subsequently titrated in Sf9 cells by using as readout the microscopic detection of GFP in the highest of triplicate endpoint dilutions.

Example 3

Production and Purification of the 1918 VLP Vaccine

Figure 2:
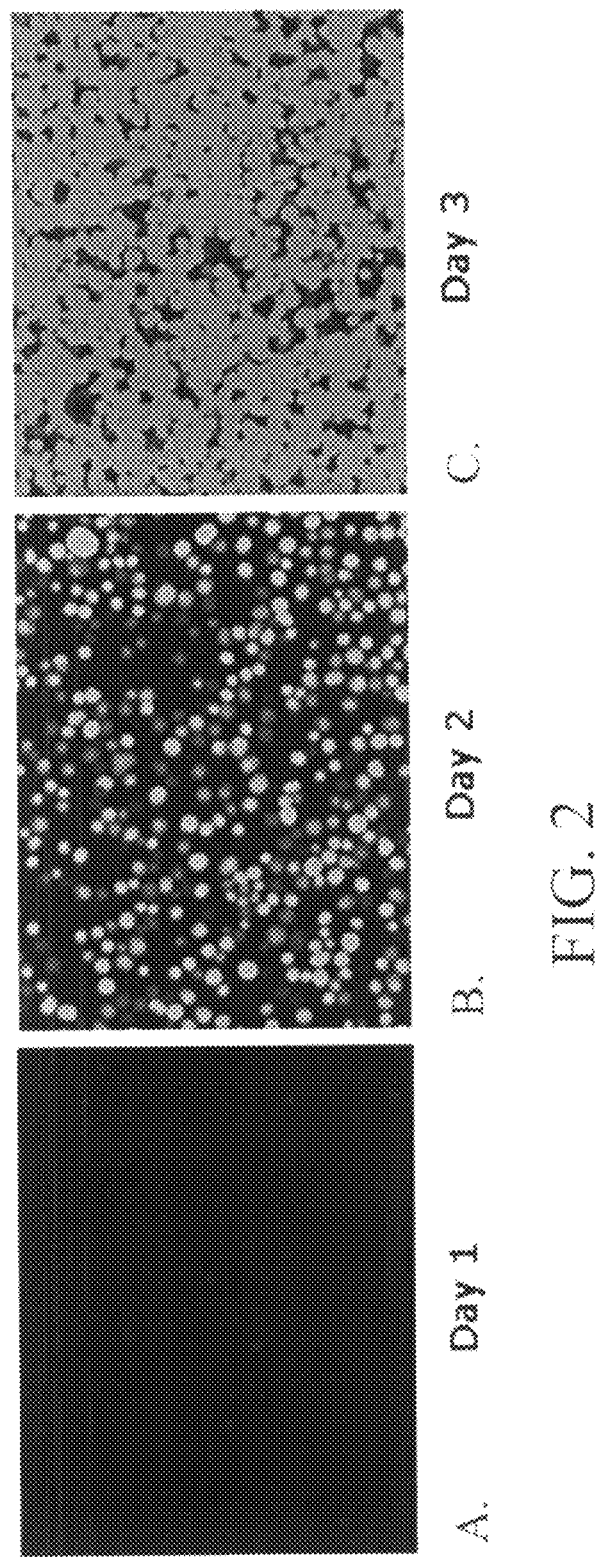
FIG. 2, panels A, B and C, show production of 1918 VLPs by infected Sf9 cells as monitored by expression of the green fluorescence protein (GFP) (shown as light spots on dark background) at day 1 (panel A), day 2 (panel B), and day 3 (panel C), post infection. The quadruple baculovirus recombinant expresses GFP in addition to the four influenza proteins required for VLP assembly; therefore GFP expression served as an indicator of infection and VLP protein production.

Sf9 cells were grown in shaker flasks with serum-free medium at 28° C. For vaccine production, cells were infected with the recombinant baculovirus at a multiplicity of infection (MOI) of 1, in ¹⁄₁₀ of the final culture volume. Virus absorption to cells was allowed for 1 hour at which point fresh medium was added to bring the culture to its final volume. Progression of the infection was monitored by taking cell samples and observing, under the microscope, the expression of the GFP by fluorescence microscopic examination of infected cells was performed at 20, 40 and 60 h post infection to determine the percentage of cells expressing GFP and the intensity of the GFP signal. Because the GFP gene is carried within the genome of the recombinant virus that expresses the VLP forming proteins, its expression denotes production of the 1918 VLP vaccine by the infected cells (FIG. 2).

After 96 hours post infection, the culture supernatant, which contains the vaccine, was separated from the cells by low speed centrifugation (2000×g for 15 min at 4° C.). Then, the vaccine particles were pelleted by centrifugation of the supernatant at 200,000×g for 90 min. Depending on the number of cells initially infected, the vaccine pellet was resuspended in 0.5 or 1 ml of 1× phosphate buffered saline (PBS), homogenized by a brief sonication and then loaded on top of an iodixanol (Optiprep, Nycomed) gradient (density of 1.08 to 1.32 g/ml). The gradient was spun at 200,000×g for 3 h and the vaccine particles under these conditions form a band within the top ⅓ of the gradient from where they were collected. See, Latham & Galarza (2001) *J. Virol.* 75(13):6154-6165; Galarza et al. (2005) *Viral. Immunol.* 18(1):244-51; and U.S. Patent Publication 20050186621. Vaccine particles were dialyzed in 1×PBS and this preparation was used as VLP vaccine with and without adjuvant.

Example 4

Western Blot Analysis of Purified VLP Vaccine

Purified vaccine material was analyzed by Western blot to confirm the presence of specific proteins and determine the HA content as previously performed essentially as described in Galarza et al. (2005) *Viral. Immunol.* 18(1):244-51. Briefly, the protein content of the 1918 VLP vaccine was evaluated with antibodies to the 1918 HA and M1 proteins. A mouse monoclonal anti-1918 HA antibody was used as primary antibody to detect the 1918 HA. Rabbit anti-mouse horseradish peroxidase conjugated (BioRad, Hercules, Calif.) was used as secondary antibody. Similarly, a mouse polyclonol anti-M1 antibody (AbD Serotec, Raleigh, N.C.) was used to detect the M1 protein, which was derived from the influenza A/Udorn/72. The M1 and M2 proteins share nine amino acids at their NH2 terminals and a band of the size expected for the M2 protein was observed with very high levels of VLP and M1 antibody.

Figure 3:
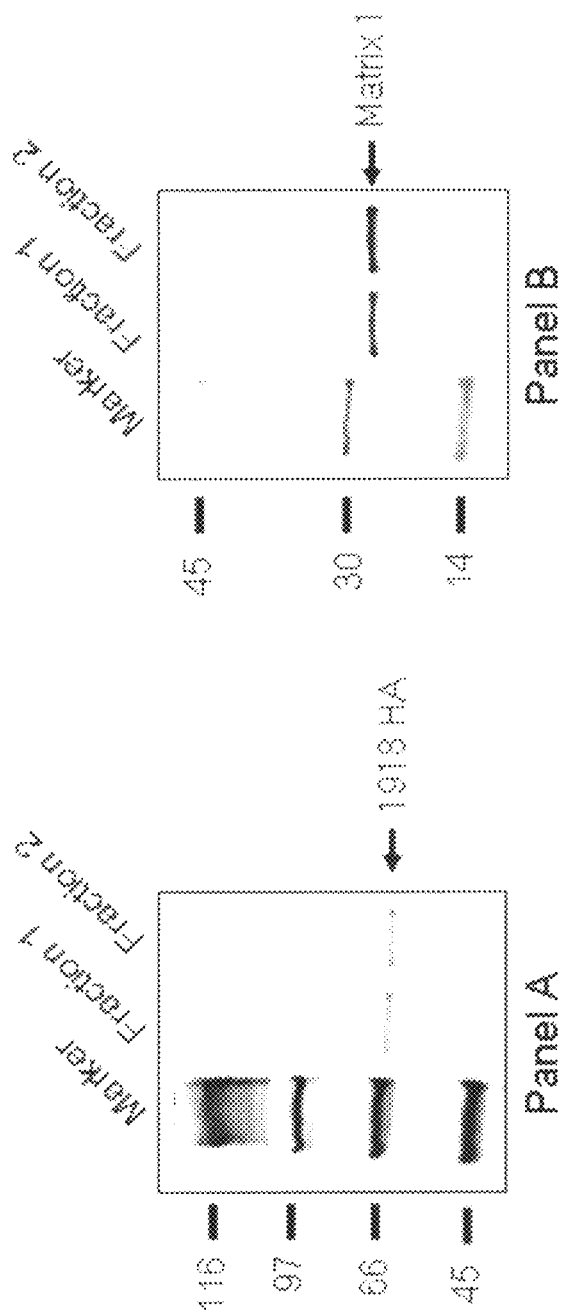
FIG. 3, panels A and B, depict Western blot analysis of gradient purified 1918 VLP vaccine. The top two fractions of the gradient were collected and analyzed by Western blot using as primary antibodies an anti-1918 HA (panel A) mouse monoclonal and an anti-M1 (panel B) mouse polyclonal (Serotec, N.Y.). Both proteins were detected in the purified VLP vaccine fractions.
Figure 5:
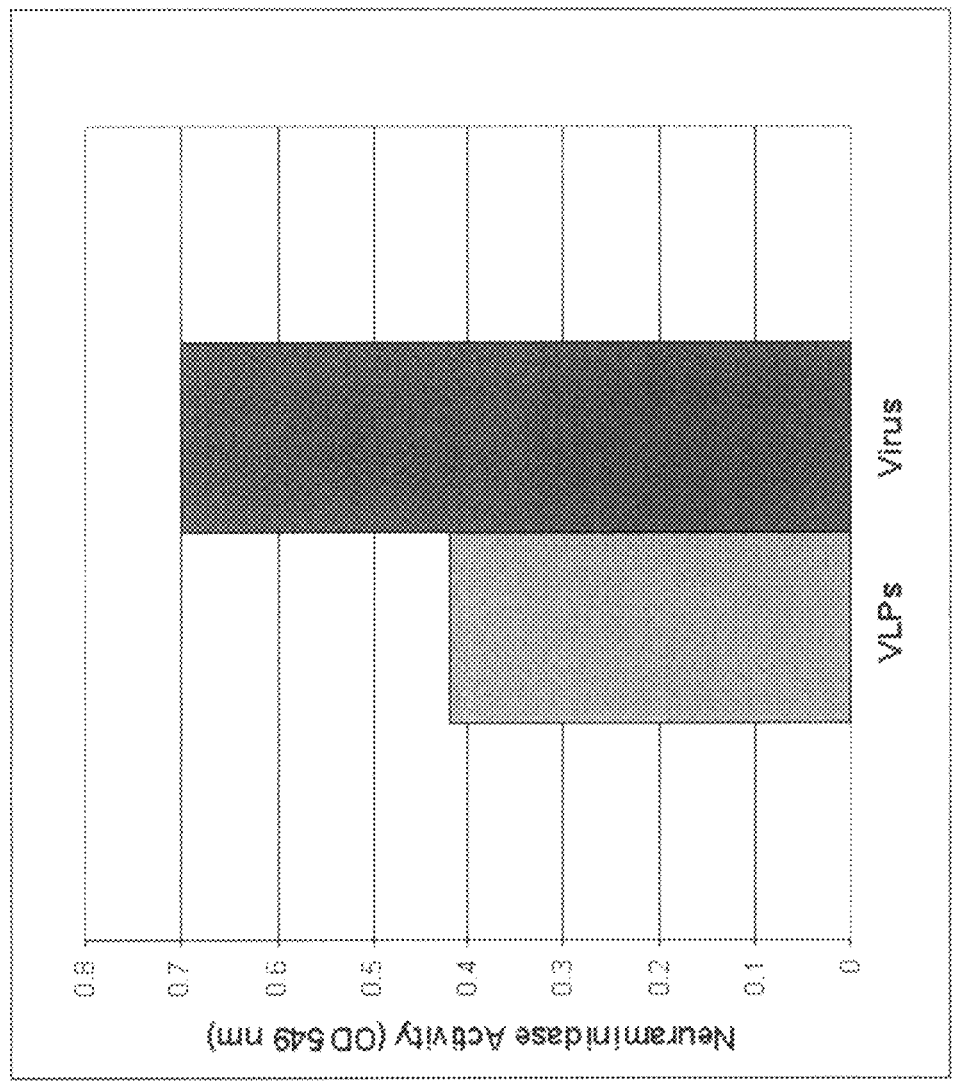
FIG. 5 is a graph depicting neuraminidase activity (expressed as the optical density (OD) at wavelength 549 nm) of purified VLPs as assayed in an enzymatic reaction using fetuin as a substrate.

Western blot analyses demonstrated that the 1918 HA protein was present in the purified 1918 VLP vaccine fractions (FIG. 3, panel A). When an antibody to the M1 protein was used in Western blot, it was demonstrated that M1 protein was present in the same two VLP vaccine fractions as the HA (FIG. 3, panel B). The M2 protein was detected when higher concentrations of purified material were loaded in the gel (Data not shown). Expression and incorporation of the NA protein was evaluated in purified VLPs by a neuraminidase assay (FIG. 5), which showed that NA was indeed incorporated into the VLP as previously shown by immunofluorescence and immunogold labeled electron microscopy with another VLP (Latham & Galarza (2001) *J. Virol.* 75(13): 6154-6165).

Example 5

Neuraminidase Assay

The presence of neuraminidase (NA) was evaluated by detecting its enzymatic activity (sialidase) which cleaves the terminal sialic acid residues from glycoproteins essentially as described in the *WHO manual on animal influenza diagnosis and surveillance. Global Influenza Programme. Geneva, World Health Organization.* 2002: p. 40-47. Purified VLPs were incubated with fetuin as substrate for 16 hours at 37° C. The amount of free sialic acid released from the substrate by the enzymatic activity of the NA was detected with thiobarbituric acid which produces a pink color in proportion to the amount of free sialic acid in the assay. A reaction with PBS and fetuin was carried out as control and used as blank in the spectrophotometric readings. Influenza A/swine virus was tested as positive control. Color intensity was measured spectrophotometrically at the wavelength of 549 nm. NA enzymatic activity is expressed as optical density (OD) at a 549 nm.

Example 6

VLP Vaccine Hemagglutination Assay

The ability of the 1918 VLPs vaccine to agglutinate red blood cells (RBC) was evaluated in a standard hemagglutination assay using cells from two different species, chicken and turkey. Briefly, twofold serial dilutions of the purified VLP vaccine were carried out with 1×PBS in V-shape 96 well plates. Then, an equal volume of a 0.5% solution of RBCs in 1×PBS was added to the wells and the plate incubated at 4° C. for 1 h. After this time, the appearance of a RBCs precipitate (RBCs button) indicates lack of hemagglutination. Hemagglutination titers are expressed as the inverse of the highest dilution of the vaccine able to agglutinate RBCs.

Figure 4:
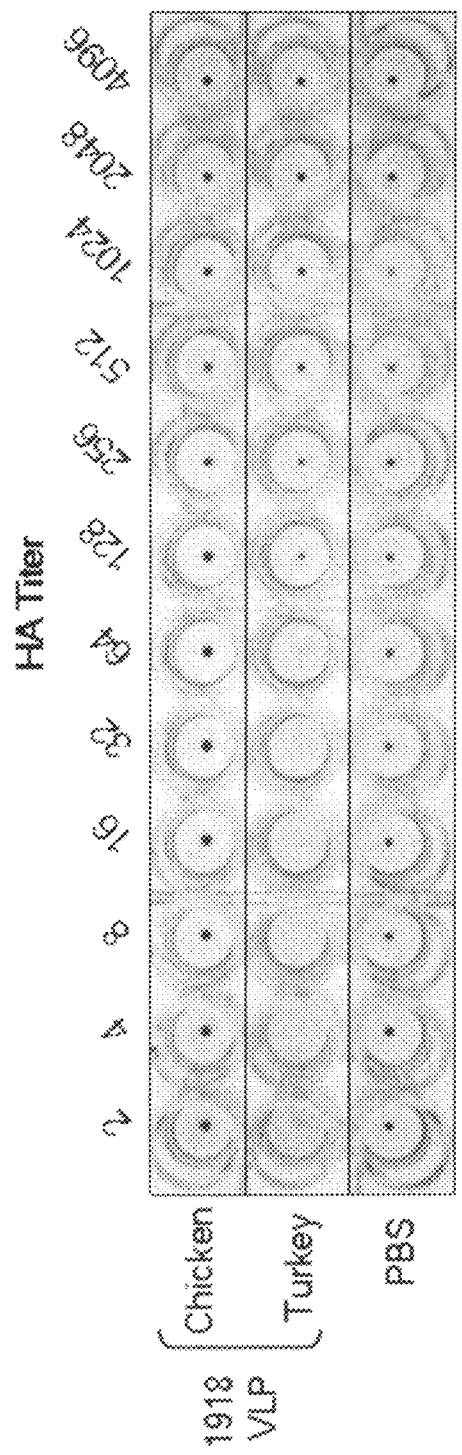
FIG. 4 shows that the 1918 VLPs agglutinate turkey red blood cells (RBC) but not chicken red blood cells, as evaluated in a standard hemagglutination assay.

Both chicken and turkey RBCs express on their surface a mixture of HA receptor with sialic acid linked to galactose by either an $\alpha$-2, 3 (SA$\alpha$-2,3) or an $\alpha$-2, 6 linkage (SA$\alpha$-2, 6). See, Iwatsuki-Horimoto et al. (2004) *J Gen Virol* 85(Pt 4): 1001-1005; Stephenson et al. (2004) *Virus Res.* 103(1-2):91-95. The 1918 VLPs were functional in hemagglutination with turkey RBCs but were not functional with chicken RBCs, even at the lower dilutions (FIG. 4).

Example 7

Generation of CHO Cells that Express the 1918 HA Proteins

As an alternative source of antigen, a CHO cell line that expresses the 1918 HA protein, was created by cloning the HA gene (see Example 1) into the plasmid pcDNA 3.1/v5-His (Invitrogen, Chicago, Ill.) by ligation into the XbaI/Kpn1 restriction sites, which were added to the ends of the synthesized HA genes by PCR. Purified recombinant plasmid DNA was transfected into CHO cells using Lipofectamine 2000 reagent (Invitrogen). Subsequently, transfected cells were cultured in serum free medium containing neomycin at the concentration of 2 mg/ml as selecting agent (a kill curve with normal CHO showed that 1 mg/ml of neomycin kill all the cells in 7 days). Cells were subcultured under selective pressure conditions for 28 days and then tested for HA 1918 expression.

Example 8

In Vivo Vaccination with Influenza VLPs

The immunogenicity and protective efficacy of the 1918 VLP vaccine was tested in 7-8 week old, female BALB/C mice (Charles River Laboratories, Wilmington, Mass.). Mice were housed in the Department of Comparative Medicine, New York Medical College and the study was carried out following institutional IACUC-approved protocols.

Four groups of 12 mice each received vaccine, placebo, and control treatment. The two vaccine groups received (via intranasal route) two doses, two weeks apart, of VLP vaccine (11 g of HA content per dose) alone or admixed with 101 g per dose of a oligonucleotide (20mer ODN). This ODN contained two CpG motifs located in the middle of the molecule and spaced by two bases (CGXXCG) and flanked by complementary sequences able to form a stem-loop structure. The placebo and control groups also received via intranasal route two doses of either PBS) or formalin inactivated influenza A/Swine/Iowa/15/30 (H1N1) (~1 µg of HA content), respectively.

Two weeks after the primary and booster immunizations, mice were anesthetized with Ketamine-Xylazine (70 mg/kg and 6 mg/kg b.w. respectively) and blood samples were collected via retro-orbital bleeding. Eighteen days after the booster immunization, mice in all groups (anesthetized as above) were challenged via the intranasal route with $1 \times 10^6$ PFU per 20 µl of the influenza virus A/Swine/Iowa/15/30 (H1N1), a surrogate for the extinct 1918 influenza virus. The influenza ASwine/Iowa/15/30 (H1N1) virus (VR-333, from ATCC, Manassas, Va.) is antigenically related and most contemporary to the 1918 influenza virus and was used as surrogate challenge. This virus was grown in 10 day-old embryonated chicken eggs (SPF, Charles River Laboratories, MA) for 48 hs post infection at 37° C. The infected allantoic fluid was harvested and clarified by low speed centrifugation and virus titer determined by the plaque assay in MDCK Cells. Aliquots of the virus were stored at −80° C. until use.

The challenge dose was delivered by small drops (10 µl per nostril) using a pipetman with an ultra slim capillary sequencing tip. Mice were monitored daily for weigh loss, clinical signs and severity of infection. On days 2, 4, 6 and 8 post-challenge, four mice from each group were euthanized and their nasal passages and trachea-lungs were harvested and placed in 1.5 ml of SPG (0.22M sucrose, 0.01M potassium phosphate, 0.005M potassium glutamate in phosphate buffered saline, pH 7.2). Tissues were homogenized for 1.5 min with an Omni International TH homogenizer equipped with a saw-tooth generator. Samples were centrifuged at 2500×g for 10 min to pellet cell debris and clarified supernatant stored at −80° C. until virus titrations were performed.

Virus load in the nasal passages and trachea/lung tissues were determined by a cell-based ELISA assay using an anti-NP antibody that recognizes the nucleoprotein (NP) of influenza A viruses. This assay is very sensitive and highly specific allowing for the detection of low levels of NP protein expressed in infected cells. MDCK cells were seeded at the concentration of $5\times10^4$ cells per well in 96 well tissue culture plates and incubated overnight at 37° C. in 5% $CO_2$. Cell monolayers were washed with PBS and infected with 100 µl of ten-fold serial dilutions in PBS of tissue homogenates. Lung/trachea and nasal tissue samples were assayed in septaplicates on the same 96 well plate. Infected plates were incubated at RT for 1 h and then the inoculum was removed and replaced with 100 µl of MEM (Minimal Essential Medium) containing 50 U/ml penicillin and 50 mg/ml streptomycin and 1 µg/ml trypsin TPCK (Worthington Biochemical, Lakewood N.J.). Subsequently, plates were incubated at 37° C. in 5% $CO_2$ for an additional 40 hours, at which time the plates were spun down at 2800×g for 12 min. and then fixed for 10 min at RT with 100 µl of an acetone/methanol (1:1) mixture.

Plates were then washed 6 times with buffer (PBS with 0.05% tween-20), blocked for 1 h at RT with 150 µl of blocking solution [5% nonfat milk, 1% bovine serum albumin (BSA) (Pierce, Rockford Ill.), 2% normal goat serum (Vector Labs, Burlingame Calif.), 0.05% tween-20 in PBS] and washed again 3 times with wash buffer. Subsequently, 100 µl of a mouse monoclonal anti-NP primary antibody (Influenza A H1N1 clone IVF8 Biodesign International, Saco, Me.; diluted 1:3000 in 1% BSA, 2% normal goat serum, 0.05% tween-20 in PBS) was added and then plates incubated for 1 h at RT. Primary antibody was not added to rows 6 and 12 so that background signals can be subtracted during virus titer calculation. Plates were again washed 3 times with wash buffer and then 100 µl of a secondary goat anti-mouse antibody conjugated with HRP (1:2500 dilution in 1% BSA, 2% normal goat serum, 0.05% tween-20 in PBS) (Bio-Rad, Hercules Calif.) was added and incubated for 1 h at RT. Again, plates were washed 6 times with wash buffer and 100 µl of Ultra-TMB (Pierce, Rockford Ill.) was added and rocked at RT until color development. The reaction was stopped by adding 10041 of a 0.2M HC1 acid solution when desired color intensity was achieved. Absorbance in each plate was measured at 450 nm with a Thermo Multiskan EX plate reader. Virus titers were expressed as $TCID_{50}$ and were calculated according to the Reed-Muench method (Reed (1938) *Am. J. Hyg.* 27:493-497.

A. Humoral Immune Response

The antibody response elicited by VLP vaccination was evaluated by ELISA using 96 well plates (Immulon II, Thermo Lab Systems, Franklin, Mass.) coated with either detergent disrupted purified influenza virus A/Swine/Iowa/15/30 (H1N1) or CHO cells expressing the 1918 HA protein as antigens (Example 7). Virus coated plates received 50 ng of total viral protein per well whereas the CHO cell based ELISA plates were seeded with an equivalent number of cells and incubated until they reached confluency at which time they were fixed with a 1:1 mixture of methanol/acetone for 10 min at RT. Both ELISA plates were blocked for 1 h at RT with PBS solution, pH 7.2, containing 1% bovine serum albumin (BSA), 2% goat serum, 2% nonfat milk and 0.05% Tween-20 and subsequently washed 3 times with PBS containing 0.05% Tween-20 (PBST). Serial dilutions of individual serum samples were applied to either of the plates and incubated for 1 h at RT, followed by three washes with the PBST solution.

Subsequently, the plates were incubated for 1 h at RT with 100 µl of a horseradish peroxidase (HRP) goat anti-mouse secondary antibody, diluted 1:1000 in PBS plus 1% BSA, 2% goat serum and 0.05% Tween-20 and this was followed by another set of three washes with PBST. Finally, the plates were incubated with 100 µl of TMB solution (Pierce, Rockford, Ill.) and monitored for color development. The color reaction was stopped by adding 100 µl of 0.1M HCL. The absorbance was determined at 450 nm using a Thermo Multiskan EX plate reader.

Absorbance titers were determined as the highest serum dilution that had an optical density twice the absorbance given by the pre-immunized control serum.

Furthermore, the 1918 HA-CHO cell based ELISA was validated by utilizing CHO cells that expressed the 1918 HA, parental CHO cells that did not expressed HA, an anti-1918 HA mouse monoclonal antibody as positive control serum (see above) and mouse pre-immunization serum as negative control. Using the two cell lines and antibodies, a standard curve was established which verified the validity of the assay.

Figure 6:
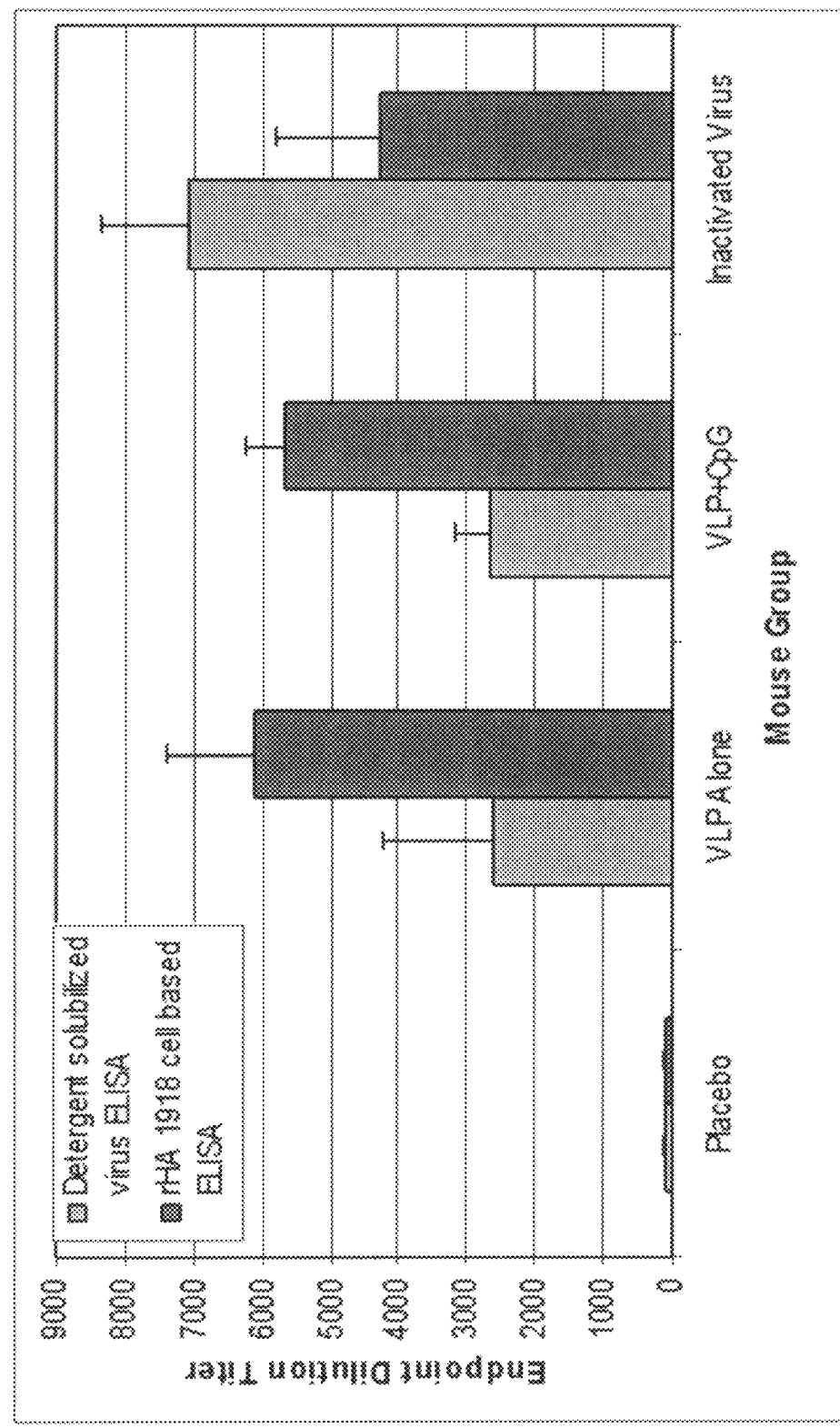
FIG. 6 is a graph depicting serum antibody responses to 1918 virus-like particles (VLPs). Light gray bars depict detergent solubilized virus ELISA while dark gray bars depict rHA 1918 cell based ELISA. Data represents the average of all the individual measurements.

As shown in FIG. 6, the 1918 VLP vaccine groups produced high levels of antibodies. When the CHO cells expressing the 1918 HA were used as antigen in the ELISA test, as also found with the disrupted virus ELISA, there was not a significant difference in the levels of serum IgG between mice immunized with the 1918 VLP vaccine alone or adjuvanted with the CpG-ODN.

Figure 10:
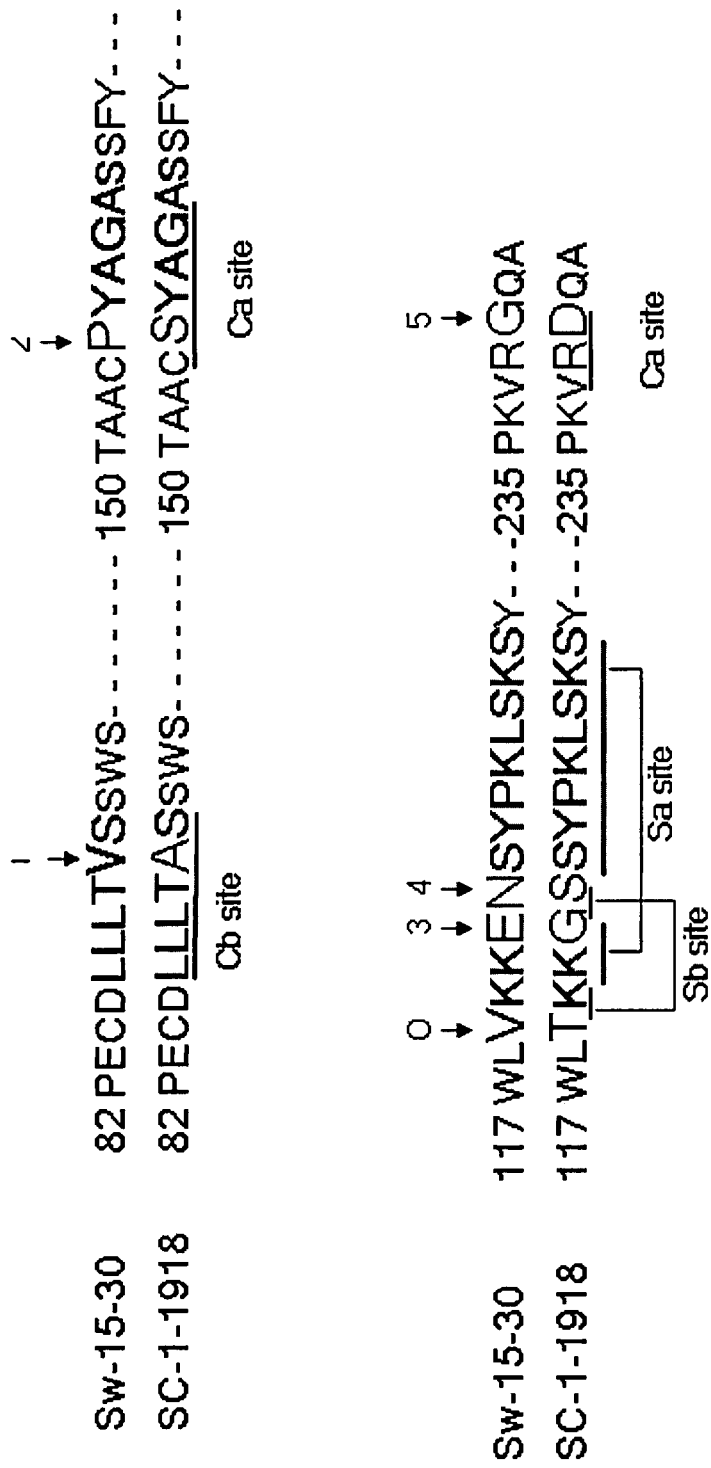
FIG. 10 is a schematic depicting amino acid differences between swine (SEQ ID NOs: 1, 3, 5 and 7) and 1918 (SEQ ID NOs: 2, 4, 6 and 8) HAs. Numbered arrows (1 to 5) above residues indicate that five of the 22 amino acid differences between the swine and 1918 virus on the HA1, mapped on the four antigenic sites, Numbered arrow "0" depicts a change adjacent to the Sb site, which change may influence the antibody interactions with this site.

In addition, mice vaccinated with the 1918 VLP vaccine with or without CpG as well as mice immunized with the inactivated virus demonstrated an antibody response when disrupted virus was used as antigen (FIG. 6). As shown in FIG. 6, CpG did not enhance the serum antibody response to the 1918 VLP vaccine. The more robust antibody response in mice immunized with inactivated virus may be due to antigenic differences between the 1918 HA, which is part of the VLP vaccine, and the HA of the swine virus which is the coating antigen for the virus ELISA (FIG. 10) and/or that the inactivated virus vaccine delivers a larger number of viral specific proteins/antigens (e.g. nucleoprotein NP) than the number of antigens present in the 1918 VLP vaccine that enhance the overall immune response in the ELISA assay.

B. Challenge with Swine Influenza

To evaluate the level of protection afforded by two doses of the 1918 VLP vaccine, formulated in PBS alone or in PBS plus CpG-ODN, inactivated virus control, and placebo inoculations, administered via intranasal route, mice in all groups were challenged seventeen days after the second immunization with 1×10⁶ PFU of influenza A/Swine/Iowa/15/30 (H1N1) virus. This influenza virus was selected as a surrogate challenge because it is the most contemporary and antigenically related to the 1918 virus currently available, other than the recently reconstructed 1918 virus (Glaser et al. (2005) *J. Virol.* 79(17):11533-11536).

Preliminary experiments in mice showed that the swine virus at the dose utilized as challenge causes severe influenza illness with typical clinical signs of the disease such as progressive inactivity beginning around day 3 post infection, ruffled fur, labored breathing, tendency to huddle and reduced or absence of water and food intake leading to severe weight loss. All these parameters were subsequently monitored during the protective efficacy study with the 1918 VLP vaccine.

Vaccinated and control mice were slightly anesthetized, as described above, prior to receiving the virus challenge (1×06 PFU), which was contained in a volume of 20 µl and administered by intranasal instillation of very small droplets delivered by ultra-slim sequence tips (10 µl per nostril). Following virus challenge, three different measurements were utilized to assess vaccine protective efficacy: body weight measurement, clinical sign of illness and virus titers in nasal and trachea/lungs tissues. Clinical signs of influenza illness were scored as: (+) no clinical sign of disease, although body weight measurement may indicate slight body mass losses; (++) ruffled fur, inactivity, tendency to huddle; (+++) hunched back, pronounced ruffled fur, severed inactivity, (++++) labored breathing (high frequency and abdominal panting) severe hunched back, ruffled fur, complete inactivity (no response to stimulation) and severed weight loss.

Figure 7:
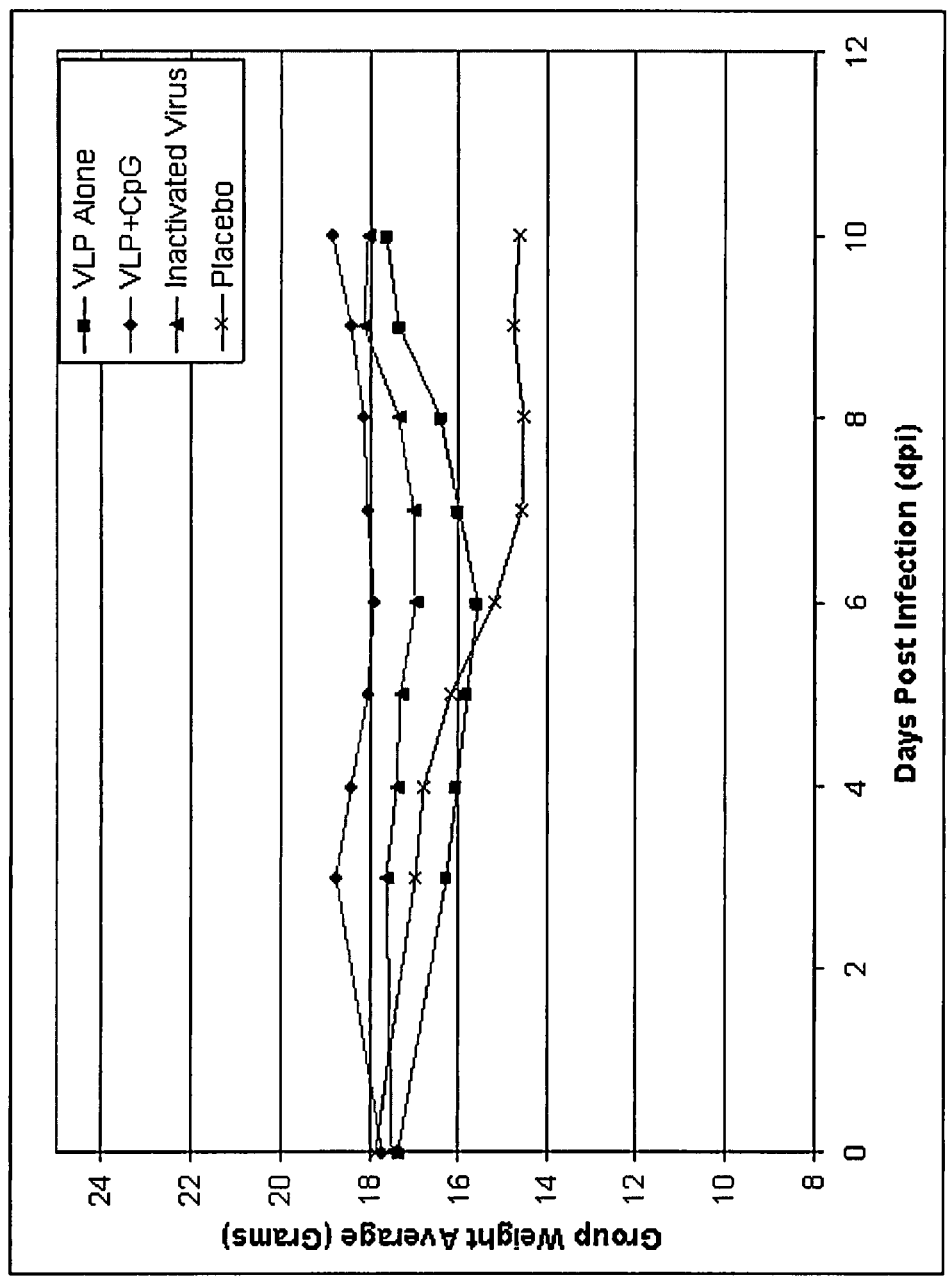
FIG. 7 is a graph depicting body weight of groups of mice following intranasal influenza challenge and presented as group weight average in grams versus days post infection. Animals who received VLP alone are shown on the line joining black squares; animals who received VLP and CpG are shown on the line joining black diamonds; animals receiving inactivated virus vaccine are shown on the line joining black triangles; and control animals (no vaccine) are shown on the line joining "x."

Group average of daily weight measurements showed that mice immunized with 1918 VLP vaccine plus CpG experienced a slight decrease in body weight between days 4 and 8 post challenge, without clinical sign of influenza infection, score (+) (FIG. 7); however the weight did not drop lower than their starting weight at day 0. The mice in the 1918 VLP vaccine alone experienced a more pronounced reduction of body weight that continued until day 6 at which point the trend reversed and mice began to gain weight. Mice in this group, however, showed very minor clinical signs of illness (score++), quite opposite to the inactivated virus control group which showed more severe clinical sign of disease (score between ++ and +++) with a less pronounced body weight loss tendency until day 6 when these mice also began gaining weight (FIG. 7). The placebo control group showed a pronounced weight loss which persisted beyond day 6 and stabilized around day 8 without a clear recovery at day 15 when the experiment was terminated. Symptoms were quite severe in this group (score++++) and one mouse died at day five post challenge. At 2, 4, 6 and 8 days post challenge, four animals per group were sacrificed and virus titers in the nasal tissue as well as in the trachea/lungs were determined in a cell based assay. Hence, the score of clinical signs and group average of body weight reported after each time point were those collected from the remaining animals in each group.

Figure 8:
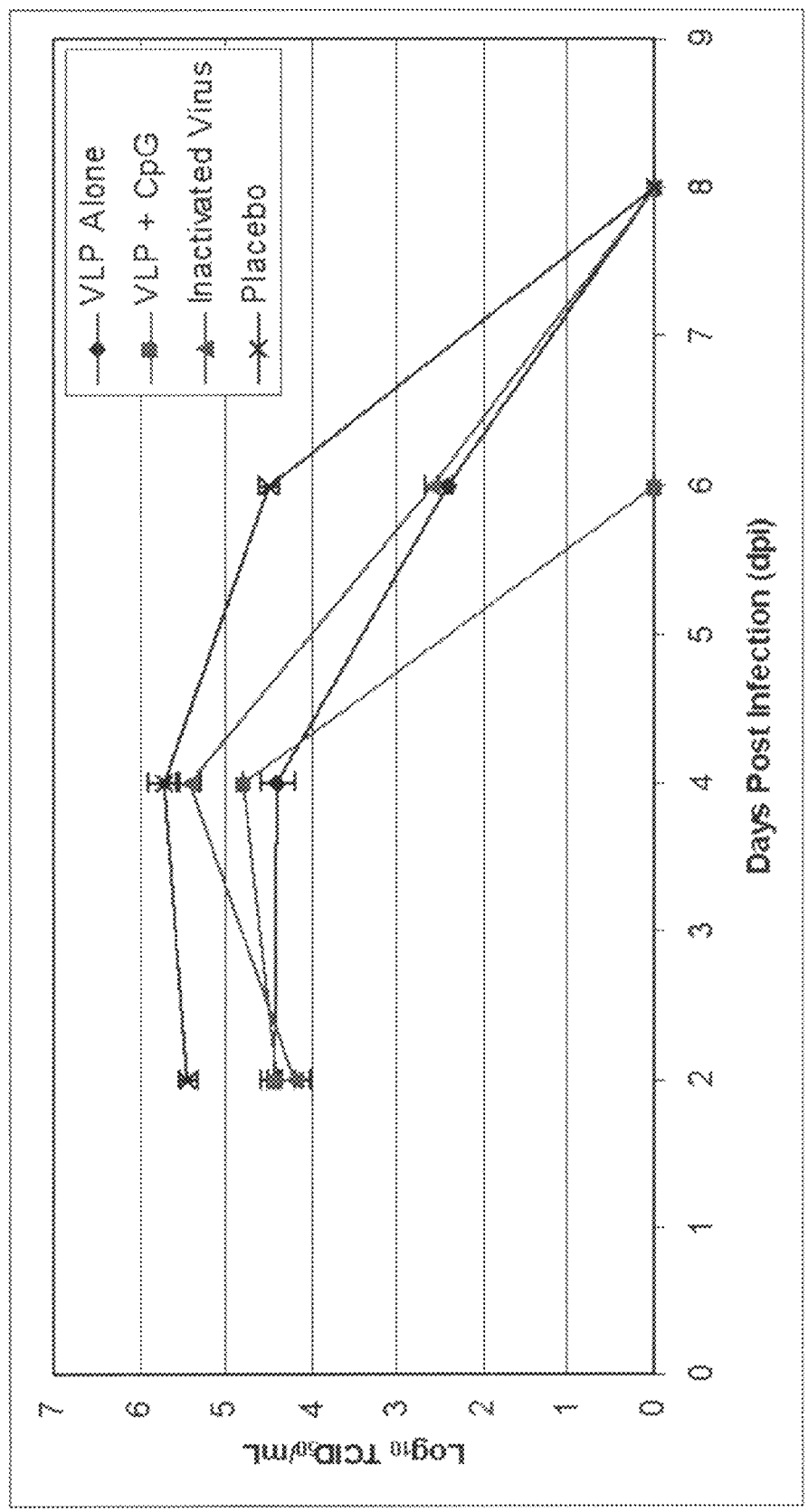
FIG. 8 is a graph depicting virus titers in nasal tissue of mice receiving VLP vaccine alone (line joining black diamonds); VLP and CpG (line joining black squares); inactivated virus vaccine (line joining black triangles) and no vaccine (placebo, line joining "x") after being intranasally challenged with $1 \times 10^6$ PFU of the influenza A/Swine/Iowa/15/30 (H1N1) virus.

Mice immunized with the 1918 VLP vaccine alone or with the 1918 VLP plus CpG had significantly lower virus titers in the nasal tissue at days 2 ($P<0.0005$), 4 ($P<0.05$) and 6 ($P<0.005$) post challenge as compared to the placebo group (FIG. 8). At day 6 post challenge, the 1918 VLP plus CpG vaccinated mice showed complete clearance of the swine virus whereas the VLP alone vaccine group still showed virus in the nasal tissue (FIG. 8). Mice immunized with the inactivated virus also had a significant lower titer than the placebo control at days 2 ($P<0.005$) and 4 ($P<0.05$) post challenge; however these titers were slightly higher on average than the virus load detected in the nose of mice immunized with either of the two 1918 VLP vaccines (FIG. 8). Virus was not detected in the nose of any of the groups at day 8 post challenge.

Figure 9:
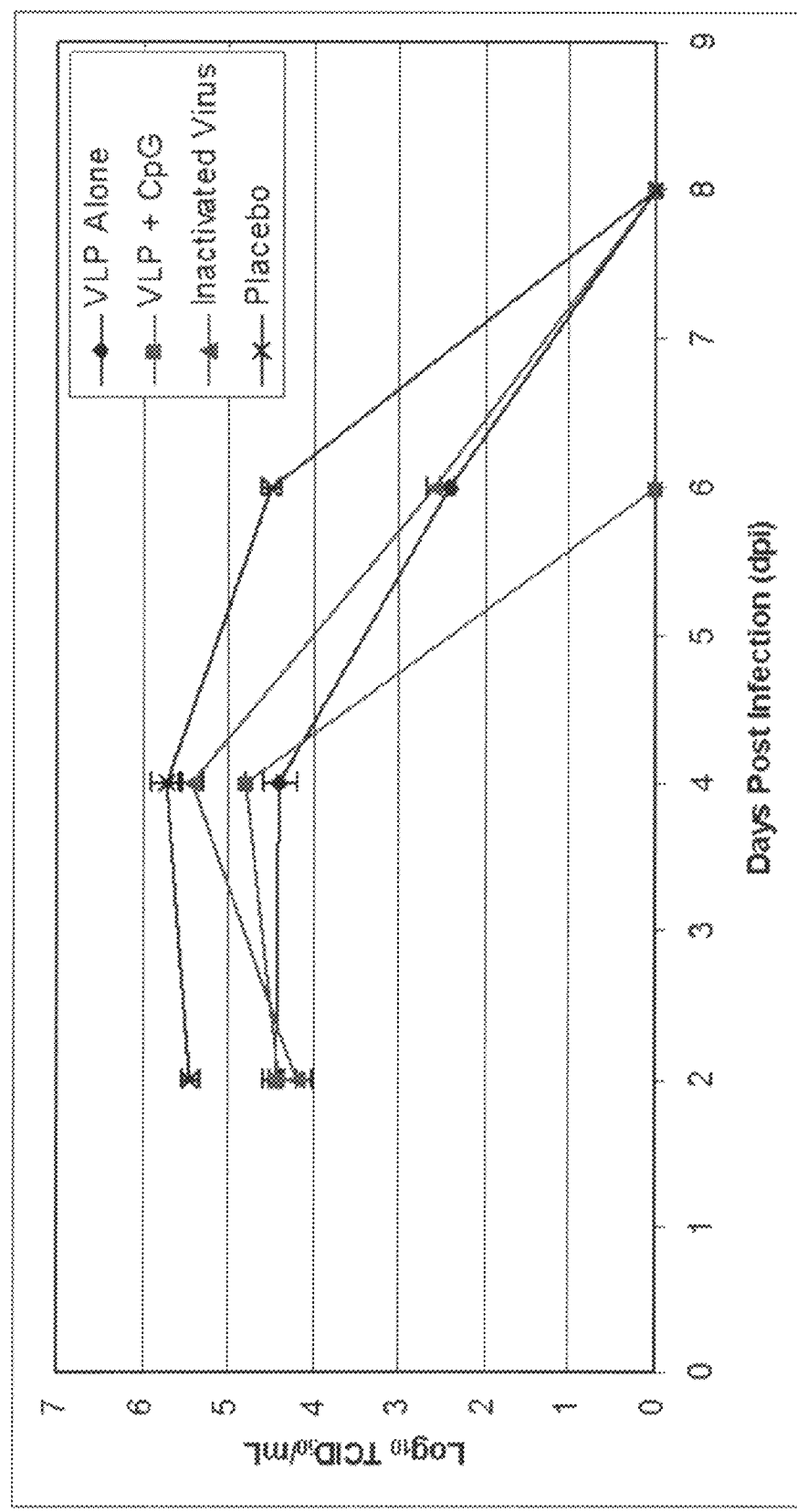
FIG. 9 is a graph depicting virus titers in trachea/lung tissue of mice receiving VLP vaccine alone (line joining black diamonds); VLP and CpG (line joining black squares); inactivated virus vaccine (line joining black triangles) and no vaccine (placebo, line joining "x") after being intranasally challenged with $1 \times 10^6$ PFU of the influenza A/Swine/Iowa/15/30 (H1N1) virus. At days 2, 4, 6 and 8 post-challenge, four animals per group were sacrificed and trachea/lungs tissues were harvested and virus titers determined by an MDCK cells based ELISA. Each time point represents the average titer of four mice and the vertical lines indicate the standard deviations values.

The level of protection of the lower respiratory track provided by either of the two 1918 VLP vaccine formulations, the inactivated virus or the placebo treatment, was also evaluated by assessing virus loads in the trachea/lungs tissues at days 2, 4, 6 and 8 post challenge. This showed that mice vaccinated with the 1918 VLP vaccine alone or 1918 VLP plus CpG, had significantly lower virus titers in the trachea/lung tissues, at days 2 ($P<0.05$), 4 ($P<0.05$) and 6 ($P<0.005$) post challenge than mice in the placebo group (FIG. 9). Furthermore, mice immunized with the 1918 VLP vaccine plus CpG were able to completely clear the viral infection from the lower respiratory track by day 6 post challenge, whereas mice in the 1918 VLP vaccine alone and inactivated virus groups still had virus at this time, although at significantly lower titers than the placebo control group. Virus titers in the trachea/lungs of mice immunized with the 1918 VLP vaccine alone were at day 4 significantly lower than that of mice immunized with the inactivated virus control, however at days 2 and 6 they showed similar levels of virus which was cleared by day 8 in both groups as well as in the placebo control.

Even though virus was detected in mice vaccinated either with the 1918 VLP alone, 1918 VLP plus CpG or inactivated swine virus vaccine, at day 2 post challenge there was a significant difference in virus titers by about a 1 or 2 log difference in the trachea/lung and nasal tissues, respectively, as compared to the placebo group. The data also indicated that the viral load was higher in the lower respiratory tract than in the upper tract but complete virus clearance occurred at day 8 post challenge in both upper and lower tracts of all the groups.

Thus, VLP vaccination conferred a significant protection against challenge with the swine virus.

What is claimed is:

1. A virus like particle (VLP) comprising an influenza matrix 1 (M1) protein, an influenza M2 protein, an influenza nucleoprotein (NP), an influenza polymerase complex protein, a first chimeric Type A influenza hemagluttinin (HA) protein and a chimeric first Type A influenza neuroamidase (NA) protein, wherein the first Type A influenza HA protein is a 1918 strain HA1 protein and the first Type A influenza NA protein is a 1918 strain NA1 protein, wherein the VLP lacks one or more of the proteins of an influenza polymerase complex, wherein the influenza proteins of the VLP are expressed from sequences encoding the proteins, and further wherein the expressed influenza proteins self-assemble into the VLP such that the influenza proteins are present in detectable amounts in the VLP and further wherein
　(i) a portion of the first influenza HA1 protein is replaced with a homologous region from a second Type A influenza HA protein, wherein the second influenza HA protein is from a different strain than the first influenza HA protein; and/or
　(ii) a portion of the first influenza NA1 protein is replaced with a homologous region from a second influenza NA protein, wherein the second influenza NA protein is from the same strain as the second HA protein.

2. The VLP of claim 1, wherein the transmembrane domain of the first HA1 or first NA1 protein is replaced with the transmembrane domain of the second HA or NA protein.

3. The VLP of claim 2, wherein the cytoplasmic tail region of the first HA or first NA protein is replaced with the cytoplasmic tail region of the second HA or NA protein.

4. The VLP of claim 3, wherein the second HA and NA proteins are derived from influenza virus A/PR/8/34 or A/Udorn/72.

5. A host cell comprising a VLP according to claim 1.

6. An immunogenic composition comprising the VLP of claim 1 and a pharmaceutically acceptable excipient.

7. The immunogenic composition of claim 6, further comprising an adjuvant.

8. A method of producing a VLP, the method comprising the steps of:
   expressing one or more polynucleotides encoding the VLP according to claim 1 in a suitable host cell under conditions such that the VLPs assemble in and are released from the host cell; and
   isolating the VLPs released from the host cell.

9. The method of claim 8, wherein the host cell is selected from the group consisting of a mammalian cell, an insect cell, a yeast cell, a plant cell and a fungal cell.

10. The method of claim 8, wherein the one or more polynucleotides are expressed from an expression vector.

11. The method of claim 10, wherein the polynucleotides are operably linked to control elements compatible with expression in the selected host cell.

12. The method of claim 11, wherein the expression vector is selected from the group consisting of a plasmid, a viral vector, a baculovirus vector and a non-viral vector.

13. The method of claim 8, wherein one or more of the polynucleotides are stably integrated into the host cell.

14. A method of generating an immune response in a subject to one or more influenza viruses, the method comprising the step of administering a composition comprising a VLP according to claim 1 to the subject.

15. The method of claim 14, wherein the composition is administered intranasally, orally, transdermally, or parentally.

16. The method of claim 14, wherein the composition is administered in a multiple dose schedule.

17. The method of claim 14, wherein an immune response to more than one influenza virus strain is generated.

* * * * *